United States Patent
Lee et al.

(10) Patent No.: US 10,307,129 B2
(45) Date of Patent: Jun. 4, 2019

(54) APPARATUS AND METHOD FOR RECONSTRUCTING TOMOGRAPHY IMAGES USING MOTION INFORMATION

(71) Applicant: SAMSUNG ELECTRONICS CO., LTD., Suwon-si (KR)

(72) Inventors: Kyoung-yong Lee, Hwaseong-si (KR); Do-il Kim, Hwaseong-si (KR); Toshihiro Rifu, Suwon-si (KR); Duhgoon Lee, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 320 days.

(21) Appl. No.: 15/228,530

(22) Filed: Aug. 4, 2016

(65) Prior Publication Data

US 2017/0055932 A1 Mar. 2, 2017

(30) Foreign Application Priority Data

Aug. 27, 2015 (KR) ........................ 10-2015-0121030

(51) Int. Cl.
*A61B 6/00* (2006.01)
*A61B 6/03* (2006.01)
(Continued)

(52) U.S. Cl.
CPC ............ *A61B 6/5264* (2013.01); *A61B 6/027* (2013.01); *A61B 6/032* (2013.01); *A61B 6/0407* (2013.01);
(Continued)

(58) Field of Classification Search
None
See application file for complete search history.

(56) References Cited

U.S. PATENT DOCUMENTS 5,966,422 A 10/1999 Dafni et al.
6,934,357 B2 8/2005 Boyd et al.
(Continued)

FOREIGN PATENT DOCUMENTS

DE 10 2011 083 647 A1 3/2013
EP 2910190 A1 8/2015
(Continued)

OTHER PUBLICATIONS

Stephane Bonnet et al., "Dynamic X-Ray Computed Tomography", Proceedings of the IEEE, vol. 91, No. 10, Oct. 2003, (1574-1587, 14 Pages Total) Digital Object Identifier(DOI): 10.1109/JPROC.2003.817868.

(Continued)

*Primary Examiner* — Tahmina N Ansari
(74) *Attorney, Agent, or Firm* — Sughrue Mion, PLLC

(57) ABSTRACT

Provided is a tomography apparatus including: a data acquisitor configured to obtain a first image by using tomography data acquired as a first X-ray generator for generating X-rays having a first energy rotates around an object over a first angular range and obtain a second image by using tomography data acquired as a second X-ray generator for generating X-rays having a second energy rotates around the object over a second angular range; a controller configured to acquire motion information representing an amount of motion of the object over time by using the first and second images; and an image reconstructor configured to reconstruct a target image showing the object at a target time point by using the motion information.

20 Claims, 17 Drawing Sheets

(51) Int. Cl.
*A61B 6/04* (2006.01)
*A61B 6/02* (2006.01)
*G06T 11/00* (2006.01)

(52) U.S. Cl.
CPC .......... *A61B 6/4007* (2013.01); *A61B 6/4447* (2013.01); *A61B 6/482* (2013.01); *A61B 6/5205* (2013.01); *G06T 11/003* (2013.01)

(56) References Cited

U.S. PATENT DOCUMENTS

| | | | |
|---|---|---|---|
| 7,630,528 B2 | 12/2009 | Kohler et al. | |
| 7,925,117 B2* | 4/2011 | Hamza | G06T 7/35 |
| | | | 382/294 |
| 8,121,368 B2* | 2/2012 | Wiersma | G06T 7/251 |
| | | | 382/128 |
| 8,548,116 B2 | 10/2013 | Flohr | |
| 9,414,788 B2 | 8/2016 | Sung et al. | |
| 2004/0230117 A1* | 11/2004 | Tosaya | A61B 17/22004 |
| | | | 600/439 |
| 2007/0242797 A1* | 10/2007 | Stewart | A61B 6/02 |
| | | | 378/16 |
| 2009/0208074 A1* | 8/2009 | Wiersma | G06T 7/251 |
| | | | 382/128 |
| 2011/0188725 A1* | 8/2011 | Yu | G06T 11/006 |
| | | | 382/131 |
| 2011/0305881 A1* | 12/2011 | Schultz | A61L 33/0088 |
| | | | 428/195.1 |
| 2014/0146937 A1 | 5/2014 | Schajer | |
| 2014/0185898 A1 | 7/2014 | Park et al. | |
| 2015/0063534 A1 | 3/2015 | Allmendinger et al. | |
| 2015/0243045 A1* | 8/2015 | Ra | A61B 6/032 |
| | | | 382/131 |
| 2017/0055932 A1* | 3/2017 | Lee | A61B 6/5264 |

FOREIGN PATENT DOCUMENTS

| | | |
|---|---|---|
| JP | 5642617 B2 | 12/2014 |
| KR | 10-1402494 B1 | 6/2014 |
| KR | 10-2014-0086627 A | 7/2014 |
| KR | 10-2014-0087213 A | 7/2014 |

OTHER PUBLICATIONS

Communication dated Jan. 17, 2017, issued by the Korean Intellectual Property Office in corresponding Korean Application No. 10-2015-0121030.

Communication dated Feb. 21, 2017, from the European Patent Office in counterpart European Application No. 16182335.6.

Communication dated Aug. 23, 2016 issued by the Korean Intellectual Property office in counterpart Korean Patent Application No. 10-2015-0121030.

* cited by examiner

FIG. 14A
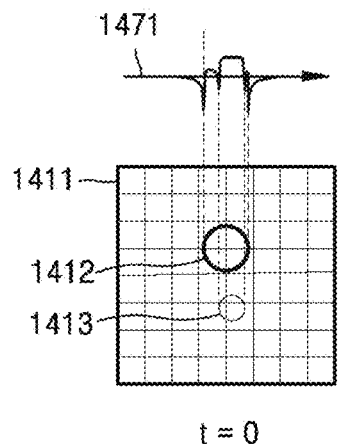
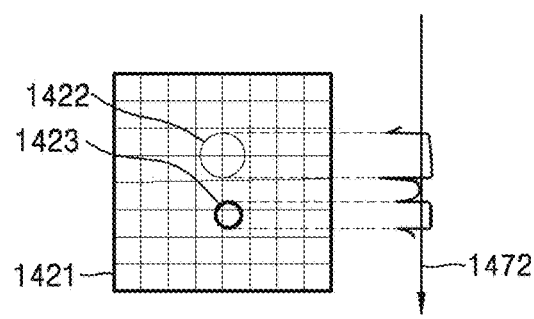
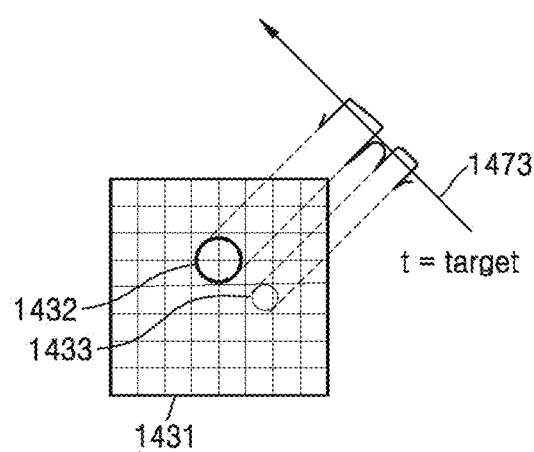
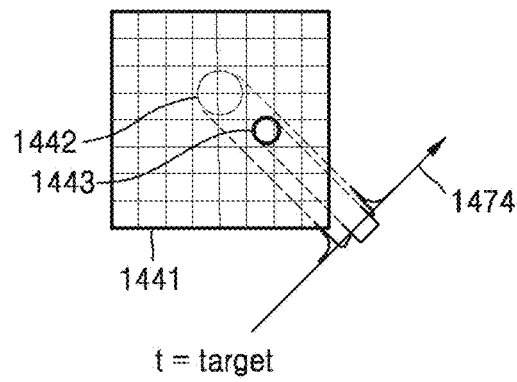
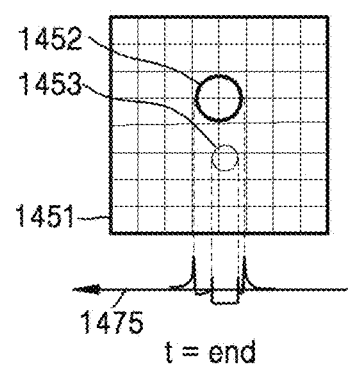
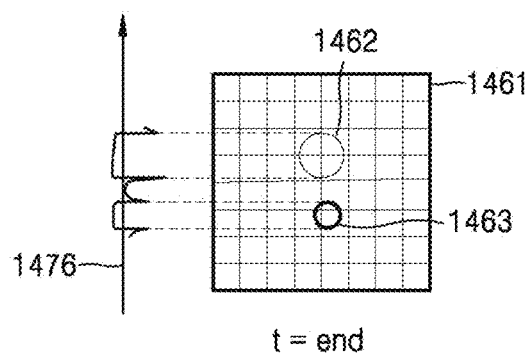
FIG. 14B

APPARATUS AND METHOD FOR RECONSTRUCTING TOMOGRAPHY IMAGES USING MOTION INFORMATION

CROSS-REFERENCE TO RELATED APPLICATION

This application claims priority from Korean Patent Application No. 10-2015-0121030, filed on Aug. 27, 2015, in the Korean Intellectual Property Office, the disclosure of which is incorporated herein in its entirety by reference.

BACKGROUND

1. Field

The present disclosure relates to tomography apparatuses and methods of reconstructing tomography images.

2. Description of the Related Art

Medical imaging apparatuses are used to acquire images showing an internal structure of an object. The medical imaging apparatuses are non-invasive examination apparatuses that capture and process images of details of structures, tissue, fluid flow, etc., inside a body and provide the images to a user. A user, e.g., a medical practitioner, may use medical images output from the medical imaging apparatuses to diagnose a patient's condition and diseases.

A computed tomography (CT) apparatus is a representative example of an apparatus for imaging an object by emitting X-rays toward a patient.

A CT apparatus is capable of providing a cross-sectional image of an object and may represent an internal structure (e.g., organs such as a kidney, a lung, etc.) of the object without superimposition of adjacent structures, as compared to a general X-ray apparatus. Due to these advantages, the CT apparatus is widely used for precise diagnosis of diseases. A medical image obtained by a tomography apparatus is hereinafter referred to as a tomography image.

A tomography apparatus performs tomography scanning on an object to acquire raw data. The acquired raw data is used to reconstruct a tomography image. The raw data may be projection data obtained by projecting an X-ray onto the object, or may be a sinogram representing a set of projection data.

For example, to obtain a tomography image, image reconstruction may be performed using a sinogram obtained by performing tomography scanning. Tomography image reconstruction will now be described in detail with reference to FIGS. 1A and 1B.

FIGS. 1A and 1B are diagrams for explaining capturing and reconstruction of a CT image.

In detail, FIG. 1A is a diagram for explaining about a CT scan performed by a CT apparatus. During the CT scan, the CT apparatus acquires raw data while rotating around an object 25. FIG. 1B is a diagram for explaining about a sinogram acquired during a CT scan and a CT image reconstructed from the sinogram.

A CT apparatus generates and emits, via an X-ray generator, an X-ray towards an object, and detects, via an X-ray detector, the X-ray that has passed through the object. The X-ray detector may also generate raw data corresponding to the detected X-ray.

In detail, referring to FIG. 1A, an X-ray generator 20 in a CT apparatus emits an X-ray towards the object 25. During a CT scan performed by the CT apparatus, the X-ray generator 20 rotates around the object 25 and acquires a plurality of raw data 30 through 32 corresponding to angles of rotation of the X-ray generator 20. In detail, the X-ray generator 20 acquires the plurality of raw data 30 through 32 by detecting X-rays emitted toward the object 25 at positions P1 through P3, respectively. In this case, raw data may be projection data.

The X-ray generator 20 has to rotate 180 degrees or greater during a CT scan in order to produce a cross-sectional CT image.

Referring to FIG. 1B, a sinogram 40 may be acquired from a combination of the plurality of the raw data 30 through 32 acquired by the X-ray generator 20 that moves at predetermined angular intervals as described with reference to FIG. 1A. The sinogram 40 is acquired by performing a CT scan as the X-ray generator 20 rotates for one period. The sinogram 40 corresponding to the one period may be used to produce a cross-sectional CT image. The one period may be a time period for the X-ray generator 20 to rotate by an angle that is greater than or equal to 180 degrees or by an angle that is greater than or equal to 360 degrees depending on specifications for a CT system.

A CT image 50 is reconstructed by performing filtered backprojection (FBP) on the sinogram 40.

In general, it takes about 0.2 seconds for the X-ray generator 20 to rotate 180 degrees.

When an object to be scanned moves, motion of an object may occur even during one period. Due to the motion of the object, motion artifacts occur in a reconstructed CT image.

When motion artifacts occur, an outermost edge of an object may be unclear and may overlap with itself or others in a reconstructed CT image, and an inner edge of the object may be blurred within the CT image due to motion of the object.

These motion artifacts in a CT image may reduce the quality of the CT image and accordingly, degrade the accuracy of analysis of an image and diagnosis of a disease by a user, e.g., a medical practitioner.

Thus, when a CT scan is performed on a moving object, it is of great importance to reconstruct a CT image with minimized motion artifacts.

SUMMARY

Provided are tomography apparatuses and methods of reconstructing a tomography image, whereby temporal resolution may be improved so that motion artifacts that may occur in a reconstructed tomography image are reduced and a more accurate tomography image may be reconstructed.

Provided are tomography apparatuses and methods of reconstructing a tomography image, whereby a more accurate tomography image may be reconstructed by using two sources for generating X-rays having different energies.

Provided are tomography apparatuses and methods of reconstructing a tomography image, whereby temporal resolution of a reconstructed tomography image may be improved by accurately measuring the amount of motion of an object over time based on data acquired during a tomography scan using two sources for generating X-rays having different energies and performing motion correction based on the measured amount of motion.

Additional aspects will be set forth in part in the description which follows and, in part, will be apparent from the description, or may be learned by practice of the presented exemplary embodiments.

According to an aspect of an exemplary embodiment, a tomography apparatus includes a data acquirer configured to obtain a first image using first tomography data acquired as a first X-ray generator for generating X-rays having a first energy rotates around an object over a first angular range, and to obtain a second image using second tomography data acquired as a second X-ray generator for generating X-rays having a second energy rotates around the object over a second angular range; a controller configured to determine motion information representing an amount of motion of the object over time using the first image and the second image; and an image reconstructor configured to reconstruct a target image showing the object at a target time point using the motion information.

The first image and the second image may be partial images, and the first angular range may be opposite to the second angular range.

Each of the first angular range and the second angular range may be less than 180 degrees.

The motion information may further include information representing an amount of motion of a surface forming the object.

The image reconstructor may be further configured to predict an amount of motion of the object at the target time point based on the motion information, and to reconstruct the target image based on the predicted amount of motion.

The data acquirer may be further configured to acquire two pieces of tomography data corresponding to an angular range of 180 degrees and an extra angle by respectively using the first x-ray generator and the second X-ray generator, and the extra angle may be in a range of about 30 degrees to about 70 degrees.

The image reconstructor may be further configured to reconstruct the target image based on a first reconstructed image and a second reconstructed image, the first reconstructed image and the second reconstructed image being generated based on the first tomography data and the second tomography data acquired during the rotation of the first x-ray generator and the second X-ray generator using the motion information.

The image reconstructor may be further configured to reconstruct the target image by performing image registration between the first reconstructed image and the second reconstructed image.

According to another aspect of an exemplary embodiment, a tomography apparatus includes a data acquirer configured to obtain a first partial image using first tomography data acquired as a first X-ray generator for generating X-rays having a first energy and a second X-ray generator for generating X-rays having a second energy rotate around an object over a first angular range and a second angular range, and to obtain a second partial image using second tomography data acquired as the first x-ray generator and the second X-ray generator rotate around the object over the second angular range and a third angular range opposite to the first angular range; a controller configured to acquire motion information representing an amount of motion of the object over time by using the first partial image and the second partial image; and an image reconstructor configured to reconstruct a target image showing the object at a target time point by using the motion information.

Each of the first angular range, the second angular range, and the third angular range may be less than 180 degrees.

The first x-ray generator may be spaced apart from the second X-ray generator by a 90-degree interval.

The data acquirer may be further configured to acquire the first tomography data and the second tomography data as the first x-ray generator and the second X-ray generator rotate around the object by 90 degrees and an extra angle, and the extra angle may be less than or equal to 90 degrees.

The data acquirer may be further configured to acquire third tomography data corresponding to an angular range of 180 degrees and an extra angle by using the first x-ray generator and the second X-ray generator, and the extra angle may be in a range of 30 degrees to 70 degrees.

The image reconstructor may be further configured to reconstruct the target image based on a first reconstructed image and a second reconstructed image, the first reconstructed image and the second reconstructed image being based on the first tomography data and the second tomography data acquired during rotation of the first x-ray generator and the second X-ray generator using the motion information.

The image reconstructor may be further configured to reconstruct the target image by performing image registration between the first reconstructed image and the second reconstructed image.

According to a further aspect of an exemplary embodiment, a method of reconstructing a tomography image includes obtaining a first image using first tomography data acquired as a first X-ray generator for generating X-rays having a first energy rotates around an object over a first angular range, and obtaining a second image using second tomography data acquired as a second X-ray generator for generating X-rays having a second energy rotates around the object over a second angular range; determining motion information representing an amount of motion of the object over time by using the first image and the second image; and reconstructing a target image showing the object at a target time point using the motion information.

The first image and the second image may be partial images, and the first angular range may be opposite to the second angular range.

Each of the first angular range and the second angular range may be less than 180 degrees.

The motion information may further include information representing an amount of motion of a surface forming the object.

The reconstructing of the target image may further include predicting an amount of motion of the object at the target time point based on the motion information, and reconstructing the target image based on the predicted amount of motion.

The obtaining of the first and second images may further include acquiring two pieces of tomography data corresponding to an angular range of 180 degrees and an extra angle by respectively using the first and second X-ray generators, and the extra angle may be in a range of 30 degrees to 70 degrees.

The reconstructing of the target image may further include reconstructing the target image based on a first reconstructed image and a second reconstructed image, the first reconstructed image and the second reconstructed image being generated based on the first tomography data and the second tomography data acquired during rotation of the first x-ray generator and the second X-ray generator using the motion information.

The reconstructing of the target image may further include reconstructing the target image by performing image registration between the first reconstructed image and the second reconstructed image.

According to a still further aspect of an exemplary embodiment, a method of reconstructing a tomography image includes obtaining a first partial image using first tomography data acquired as a first X-ray generator for generating X-rays having a first energy and a second X-ray generator for generating X-rays having a second energy rotate around an object over a first angular range and a second angular range, and obtaining a second partial image using second tomography data acquired as the first x-ray generator and the second X-ray generator rotate around the object over the second angular range and a third angular range opposite to the first angular range; acquiring motion information representing an amount of motion of the object over time by using the first partial image and the second partial image; and reconstructing a target image showing the object at a target time point by using the motion information.

Each of the first angular range, the second angular range, and the third angular range may be less than 180 degrees.

The first x-ray generator may be spaced apart from the second X-ray generator by a 90-degree interval.

The obtaining of the first partial image and the second partial image may further include acquiring the first tomography data and the second tomography data as the first x-ray generator and the second X-ray generator rotate around the object by 90 degrees and an extra angle, and the extra angle may be less than or equal to 90 degrees.

The obtaining of the first partial image and the second partial image may further include acquiring two pieces of tomography data corresponding to an angular range of 180 degrees and an extra angle by using the first and second X-ray generators, and the extra angle may be in a range of 30 degrees to 70 degrees.

The reconstructing of the target image may further include reconstructing the target image based on a first reconstructed image and second reconstructed image generated based on the first tomography data and the second tomography data acquired during rotation of the first x-ray generator and the second X-ray generator using the motion information.

The reconstructing of the target image may further include reconstructing the target image by performing image registration between the first reconstructed image and the second reconstructed image.

BRIEF DESCRIPTION OF THE DRAWINGS

These and/or other aspects will become apparent and more readily appreciated from the following description of the exemplary embodiments, taken in conjunction with the accompanying drawings in which:

FIGS. 14A and 14B are diagrams for explaining about a process of reconstructing a tomography image according to an exemplary embodiment;

DETAILED DESCRIPTION

Figure 1A:
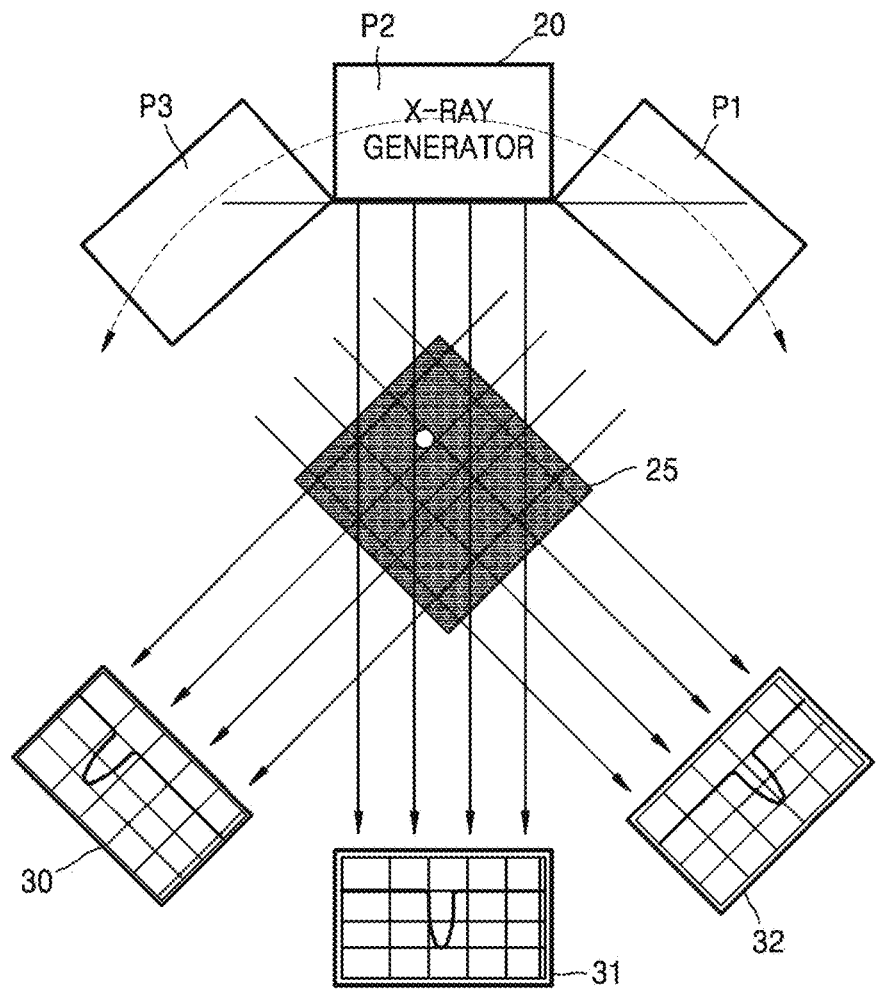
FIGS. 1A and 1B are diagrams for explaining about capturing and reconstruction of a computed tomography (CT) image.
Figure 1B:
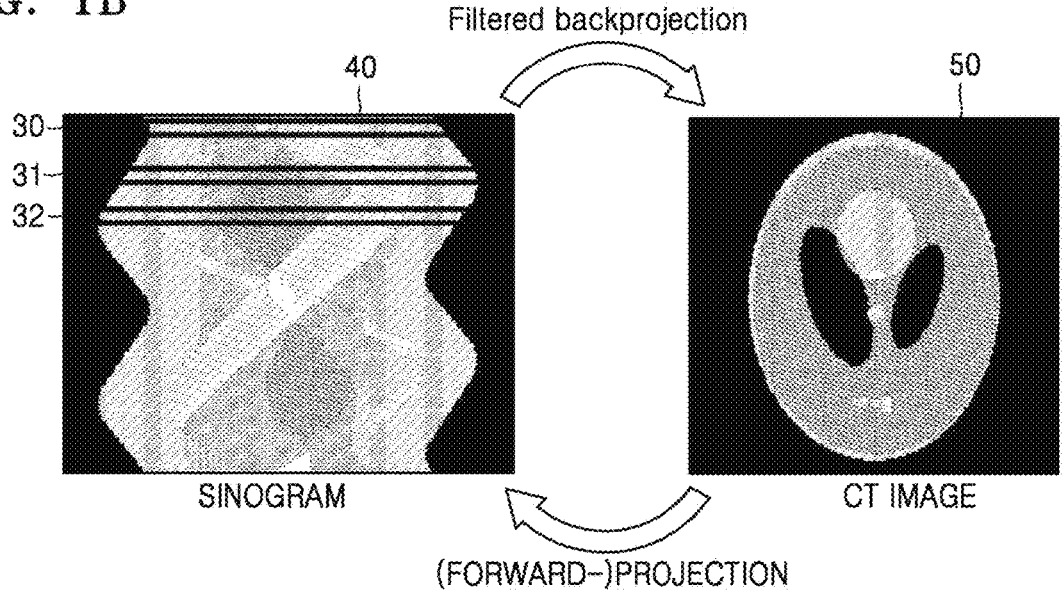

The attached drawings for illustrating exemplary embodiments of the present disclosure are referred to in order to gain a sufficient understanding of the present disclosure, the merits thereof, and the objectives accomplished by the implementation of the present disclosure. In this regard, the present exemplary embodiments may have different forms and should not be construed as being limited to the descriptions set forth herein. Rather, these exemplary embodiments are provided so that this disclosure will be thorough and complete and will fully convey the concept of the present exemplary embodiments to one of ordinary skill in the art, and the present disclosure will only be defined by the appended claims. Like reference numerals refer to like elements throughout the specification.

Hereinafter, the terms used in the specification will be briefly described, and then the present disclosure will be described in detail.

The terms used in this specification are those general terms currently widely used in the art, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of exemplary embodiments.

When a part "includes" or "comprises" an element, unless there is a particular description contrary thereto, the part can further include other elements, not excluding the other elements. Also, the term "unit" in the exemplary embodiments means a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

Reference will now be made in detail to exemplary embodiments, examples of which are illustrated in the accompanying drawings. In this regard, the present exemplary embodiments may have different forms and should not be construed as being limited to the descriptions set forth herein. In the following description, well-known functions or constructions are not described in detail so as not to obscure the exemplary embodiments with unnecessary detail. Expressions such as "at least one of," when preceding a list of elements, modify the entire list of elements and do not modify the individual elements of the list.

Throughout the specification, an "image" may mean multi-dimensional data formed of discrete image elements, e.g., pixels in a two-dimensional (2D) image and voxels in a three-dimensional (3D) image. For example, the image may include a medical image of an object which is captured by a computed tomography (CT) imaging apparatus.

Throughout the specification, a "CT image" may mean an image generated by synthesizing a plurality of X-ray images that are obtained by photographing an object while a CT imaging apparatus rotates around at least one axis with respect to the object.

Furthermore, in the present specification, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to the physical body.

Throughout the specification, a "user" may be, but is not limited to, a medical expert including a medical doctor, a nurse, a medical laboratory technologist, a medial image expert, or a technician who repairs a medical apparatus.

Because a CT system is capable of providing a cross-sectional image of an object, the CT system may distinctively express an inner structure, e.g., an organ such as a kidney or a lung, of the object, compared to a general X-ray imaging apparatus.

The CT system may obtain a plurality of pieces of image data with a thickness not more than 2 mm several hundred times per second and then may process the plurality of pieces of image data, so that the CT system may provide a relatively accurate cross-sectional image of the object. According to the related art, only a horizontal cross-sectional image of the object can be obtained, but this issue has been overcome due to various image reconstruction methods. Examples of 3D image reconstruction methods are as below:

Shade surface display (SSD)—an initial 3D imaging method of displaying only voxels having a predetermined Hounsfield Units (HU) value.

Maximum intensity projection (MIP)/minimum intensity projection (MinIP)—a 3D imaging method of displaying only voxels having the greatest or smallest HU value from among voxels that construct an image.

Volume rendering (VR)—an imaging method capable of adjusting a color and transmittance of voxels that constitute an image, according to areas of interest.

Virtual endoscopy—a method that allows endoscopy observation in a 3D image that is reconstructed by using the VR method or the SSD method.

Multi-planar reformation (MPR)—a method of reconstructing an image into a different cross-sectional image. A user may reconstruct an image in any desired direction.

Editing—a method of editing adjacent voxels so as to allow a user to easily observe an area of interest in volume rendering.

Voxel of interest (VOI)—a method of displaying only a selected area in volume rendering.

A CT system 100 according to an exemplary embodiment will now be described with reference to FIGS. 2 and 3. The CT system 100 may include various types of devices.

Figure 2:
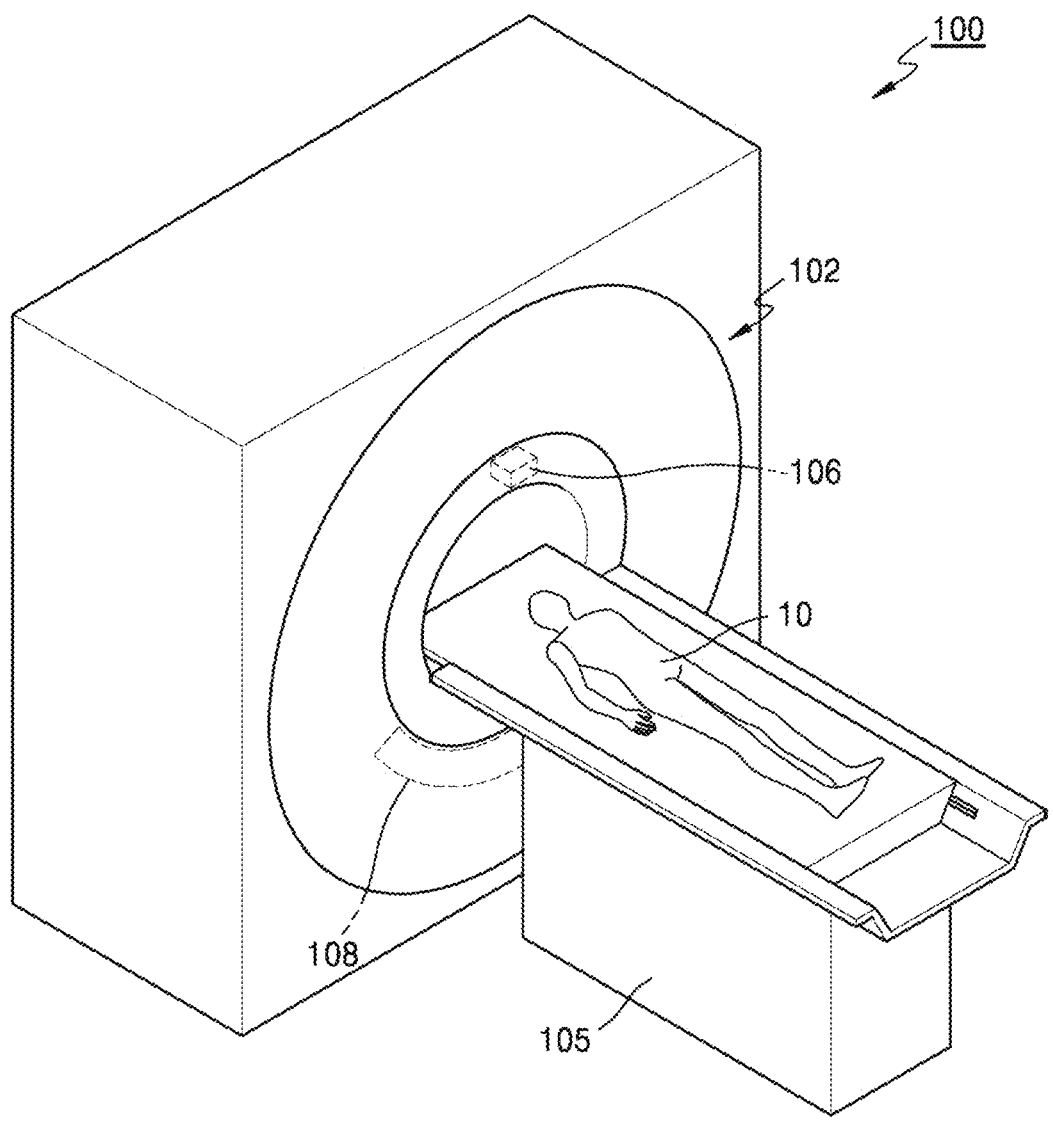
FIG. 2 is a schematic diagram of a general CT system.

FIG. 2 schematically illustrates the CT system 100. Referring to FIG. 2, the CT system 100 may include a gantry 102, a table 105, an X-ray generator 106, and an X-ray detector 108.

The gantry 102 may include the X-ray generator 106 and the X-ray detector 108.

An object 10 may be positioned on the table 105.

The table 105 may move in a predetermined direction (e.g., at least one of up, down, right, and left directions) during a CT imaging procedure. Also, the table 105 may tilt or rotate by a predetermined angle in a predetermined direction.

The gantry 102 may also tilt by a predetermined angle in a predetermined direction.

Figure 3:
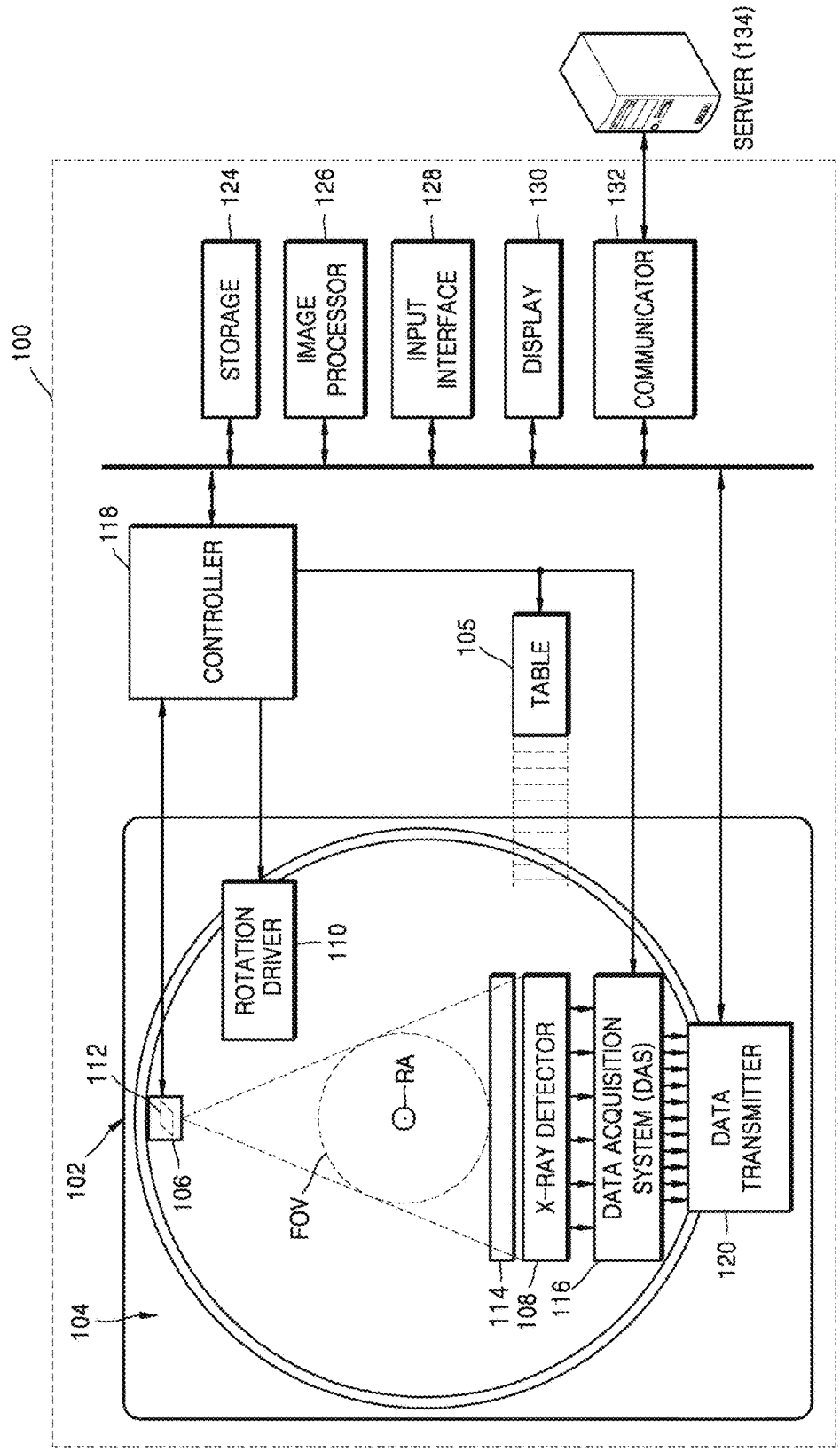
FIG. 3 shows a structure of a CT system according to an exemplary embodiment.

FIG. 3 is a block diagram illustrating a structure of the CT system 100.

The CT system 100 may include the gantry 102, the table 105, a controller 118, a storage 124, an image processor 126, an input interface 128, a display 130, and a communicator 132.

As described above, the object 10 may be positioned on the table 105. In the present exemplary embodiment, the table 105 may move in a predetermined direction (e.g., at least one of up, down, right, and left directions), and movement of the table 105 may be controlled by the controller 118.

The gantry 102 may include a rotating frame 104, the X-ray generator 106, the X-ray detector 108, a rotation driver 110, a data acquisition system (DAS) 116, and a data transmitter 120.

The gantry 102 may include the rotating frame 104 having a loop shape capable of rotating with respect to a predetermined rotation axis RA. Also, the rotating frame 104 may have a disc shape.

The rotating frame 104 may include the X-ray generator 106 and the X-ray detector 108 that are arranged to face each other so as to have predetermined fields of view FOV. The rotating frame 104 may also include an anti-scatter grid 114. The anti-scatter grid 114 may be positioned between the X-ray generator 106 and the X-ray detector 108.

In a medical imaging system, X-ray radiation that reaches a detector (or a photosensitive film) includes not only attenuated primary radiation that forms a valuable image but also scattered radiation that deteriorates the quality of an image. In order to transmit most of the primary radiation and to attenuate the scattered radiation, the anti-scatter grid 114 may be positioned between a patient and the detector (or the photosensitive film).

For example, the anti-scatter grid 114 may be formed by alternately stacking lead foil strips and an interspace material such as a solid polymer material, solid polymer, or a fiber composite material. However, formation of the anti-scatter grid 114 is not limited thereto.

The rotating frame 104 may receive a driving signal from the rotation driver 110 and may rotate the X-ray generator 106 and the X-ray detector 108 at a predetermined rotation speed. The rotating frame 104 may receive the driving signal and power from the rotation driver 110 while the rotating frame 104 contacts the rotation driver 110 via a slip ring. Also, the rotating frame 104 may receive the driving signal and power from the rotation driver 110 via wireless communication.

The X-ray generator 106 may receive a voltage and current from a power distribution unit (PDU) via a slip ring and then a high voltage generating unit, and may generate and emit an X-ray. When the high voltage generating unit applies predetermined voltage (hereinafter, referred to as a tube voltage) to the X-ray generator 106, the X-ray generator 106 may generate X-rays having a plurality of energy spectra that correspond to the tube voltage.

The X-ray generated by the X-ray generator 106 may be emitted in a predetermined form due to a collimator 112.

The X-ray detector 108 may be positioned to face the X-ray generator 106. The X-ray detector 108 may be positioned to face the X-ray generator 106. Each of the plurality of X-ray detecting devices may establish one channel but one or more exemplary embodiments are not limited thereto.

The X-ray detector 108 may detect the X-ray that is generated by the X-ray generator 106 and that is transmitted through the object 10, and may generate an electrical signal corresponding to intensity of the detected X-ray.

The X-ray detector 108 may include an indirect-type X-ray detector for detecting radiation after converting the radiation into light, and a direct-type X-ray detector for detecting radiation after directly converting the radiation into electric charges. The indirect-type X-ray detector may use a scintillator. Also, the direct-type X-ray detector may use a photon counting detector. The DAS 116 may be connected to the X-ray detector 108. Electrical signals generated by the X-ray detector 108 may be acquired by the DAS 116. Electrical signals generated by the X-ray detector 108 may be acquired by wire or wirelessly by the DAS 116. Also, the electrical signals generated by the X-ray detector 108 may be provided to an analog-to-digital converter via an amplifier.

According to a slice thickness or the number of slices, only some of a plurality of pieces of data collected by the X-ray detector 108 may be provided to the image processor 126 via the data transmitter 120, or the image processor 126 may select only some of the plurality of pieces of data.

Such a digital signal may be provided to the image processor 126 via the data transmitter 120. The digital signal may be provided to the image processor 126 by wire or wirelessly.

The controller 118 may control an operation of each of the elements in the CT system 100. For example, the controller 118 may control operations of the table 105, the rotation driver 110, the collimator 112, the DAS 116, the storage 124, the image processor 126, the input interface 128, the display 130, the communicator 132, or the like.

The image processor 126 may receive data acquired by the DAS 116 (e.g., raw data that is data before processing), via the data transmitter 120, and may perform pre-processing.

The pre-processing may include, for example, a process of correcting a sensitivity irregularity between channels and a process of correcting signal loss due to a rapid decrease in signal strength or due to the presence of an X-ray absorbing material such as metal.

Data output from the image processor 126 may be referred to as raw data or projection data. The projection data may be stored in the storage 124 with imaging conditions (e.g., the tube voltage, an imaging angle, etc.) during the acquisition of data.

The projection data may be a group of data values that correspond to the intensity of the X-ray that has passed through the object 10. For convenience of description, a group of a plurality of pieces of projection data that are simultaneously obtained from all channels at the same imaging angle is referred to as a projection data set.

The storage 124 may include at least one storage medium from among a flash memory-type storage medium, a hard disk-type storage medium, a multimedia card micro-type storage medium, card-type memories (e.g., an SD card, an XD memory, and the like), random access memory (RAM), static random access memory (SRAM), read-only memory (ROM), electrically erasable programmable ROM (EEPROM), programmable ROM (PROM), magnetic memory, a magnetic disc, and an optical disc.

The image processor 126 may reconstruct a cross-sectional image of the object 10 by using the acquired projection data set. The cross-sectional image may be a 3D image. In other words, the image processor 126 may reconstruct a 3D image of the object 10 by using a cone beam reconstruction method or the like, based on the acquired projection data set.

The input interface 128 may receive an external input with respect to an X-ray tomography imaging condition, an image processing condition, or the like. For example, the X-ray tomography imaging condition may include tube voltages, an energy value setting with respect to a plurality of X-rays, a selection of an imaging protocol, a selection of an image reconstruction method, a setting of a FOV area, the number of slices, a slice thickness, a parameter setting with respect to image post-processing, or the like. Also, the image processing condition may include a resolution of an image, an attenuation coefficient setting for the image, setting for an image combining ratio, or the like.

The input interface 128 may include a device for receiving a predetermined input from an external source. For example, the input interface 128 may include a microphone, a keyboard, a mouse, a joystick, a touch pad, a touch pen, a voice recognition device, a gesture recognition device, or the like.

The display 130 may display an X-ray image reconstructed by the image processor 126.

Exchanges of data, power, or the like between the aforementioned elements may be performed by using at least one of wired communication, wireless communication, and optical communication.

The communicator 132 may perform communication with an external device, an external medical apparatus, etc. via a server 134 or the like. The communication will now be described with reference to FIG. 4.

Figure 4:
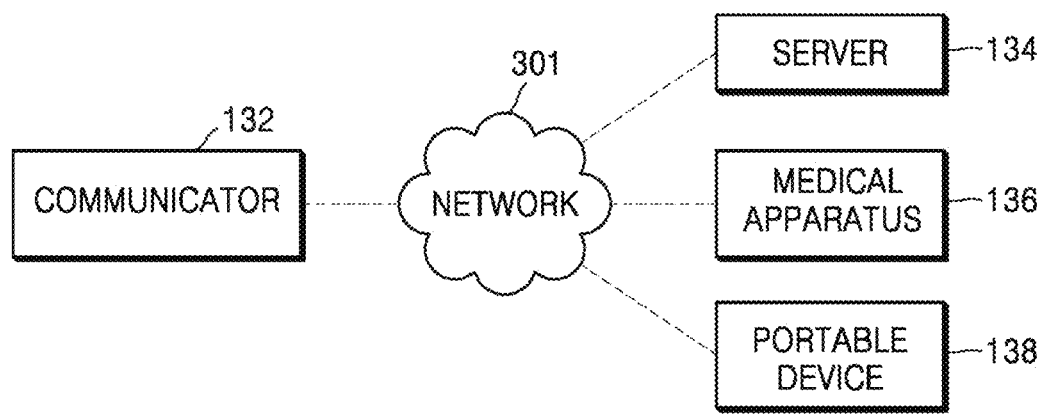
FIG. 4 is a block diagram of a configuration of a communicator.

FIG. 4 is a block diagram illustrating the communication performed by the communicator 132.

The communicator 132 may be wiredly or wirelessly connected to a network 301 and therefore may perform communication with the server 134, a medical apparatus 136, or a portable device 138. The communicator 132 may exchange data with a hospital server or other medical apparatuses in a hospital connected via a picture archiving and communication system (PACS).

Also, the communicator 132 may perform data communication with the portable device 138 or the like, according to the digital imaging and communications in medicine (DICOM) standard.

The communicator 132 may transmit and receive data related to diagnosing the object 10, via the network 301. Also, the communicator 132 may transmit and receive a medical image obtained from the medical apparatus 136 such as a magnetic resonance imaging (MRI) apparatus, an X-ray apparatus, or the like.

Furthermore, the communicator 132 may receive a diagnosis history or a medical treatment schedule about a patient from the server 134 and may use the diagnosis history or the medical treatment schedule to diagnose the patient. Also, the communicator 132 may perform data communication not only with the server 134 or the medical apparatus 136 in a hospital but also with the portable device 138 of a user or patient.

Also, the communicator 132 may transmit information about a device error, information about a quality control status, or the like to a system manager or a service manager via the network 301, and may receive a feedback regarding the information from the system manager or service manager.

Figure 5:
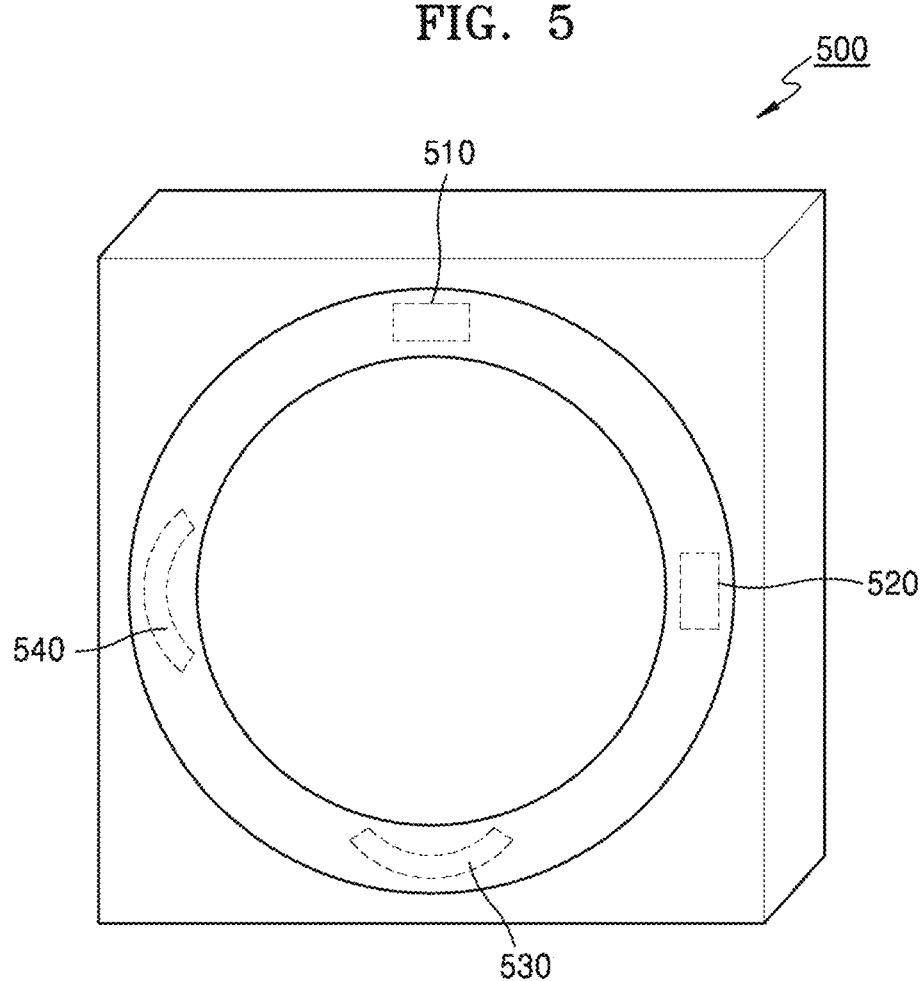
FIG. 5 illustrates a CT system according to an exemplary embodiment.

FIG. 5 illustrates a CT system 500 according to an exemplary embodiment.

Referring to FIG. 5, the CT system 500 according to the exemplary embodiment includes two X-ray generators 510 and 520, i.e., first and second X-ray generators 510 and 520, and two X-ray detectors 530 and 540 respectively corresponding to the first and second X-ray generators 510 and 520. In detail, each of the first and second X-ray generators 510 and 520 is one X-ray source. Thus, the CT system 500 including the first and second X-ray generators 510 and 520 may be a 'dual-source tomography apparatus' including the first X-ray generator 510 as one source and the second X-ray generator 520 as the other source. In detail, the X-ray detector 530 detects X-rays emitted by the first X-ray generator 510 while the X-ray detector 540 detects X-rays emitted by the second X-ray generator 520.

The first and second X-ray generators 510 and 520 may generate X-rays having an energy or energy band corresponding to a tube current and/or a tube voltage applied thereto. According to an exemplary embodiment, the first and second X-ray generators 510 and 520 may generate X-rays having the same energy. Furthermore, the first and second X-ray generators 510 and 520 may generate X-rays having different energies. In detail, when the same tube voltage or the same tube current is applied to the first and second X-ray generators 510 and 520, the first and second X-ray generators 510 and 520 generate X-rays having the same energy. Furthermore, when different tube voltages or different tube currents are respectively applied to the first and second X-ray generators 510 and 520, the first and second X-ray generators 510 and 520 may emit X-rays having different energies.

When the first and second X-ray generators 510 and 520 generate X-rays having the same energy, the CT system 500 performs a tomography scan to acquire raw data respectively as the first and second X-ray generators 510 and 520 move over different angular ranges. The acquired raw data are used to reconstruct a tomography image. Even when the two different X-ray generators, i.e., the first and second X-ray generators 510 and 520, are used, the first and second X-ray generators 510 and 520 may respectively generate X-rays having the same energy. Thus, the raw data acquired respectively through the first and second X-ray generators 510 and 520 may be used together to reconstruct a tomography image.

When raw data is acquired over certain angular ranges by using the first and second X-ray generators 510 and 520 as in the above exemplary embodiment, a raw data acquisition time may be reduced by one-half as compared to when raw data is acquired over the same angular range by using one X-ray generator. Faster raw data acquisition may shorten the total time when blurring occurs by one-half, and accordingly increase temporal resolution. High temporal resolution may reduce motion artifacts and allow reconstruction of a more accurate tomography image.

In particular, when the first and second X-ray generators 510 and 520 generate X-rays having different energies, raw data acquired using X-rays generated by each of the first and second X-ray generators 510 and 520 may be used to reconstruct a tomography image corresponding to an energy band of the X-rays used to acquire the raw data. In this case, the first and second X-ray generators 510 and 520 respectively operate as two different, independent sources. In other words, a first image corresponding to an energy band of X-rays generated by the first X-ray generator 510 may be obtained based on raw data acquired using the X-rays, and a second image corresponding to an energy band of X-rays generated by the second X-ray generator 520 may be obtained based on raw data acquired using the X-rays.

The type of a tissue or body part of an object being clearly shown in an image may vary depending on an energy band of X-rays generated by each of the first and second X-ray generators 510 and 520. For example, if a first image is obtained by using X-rays having a first energy band, fat tissue may be imaged more clearly than other tissues. On the other hand, if a second image is obtained by using X-rays having a second energy band that is different from the first energy band, soft tissue may be imaged more clearly than other tissues. Thus, by reconstructing a tomography image by using the first and second X-ray generators 510 and 520 that generate X-rays having different energies as described in the above exemplary embodiment, it is possible to reconstruct a tomography image clearly showing a particular tissue or body part that a user desires to analyze.

Figure 6:
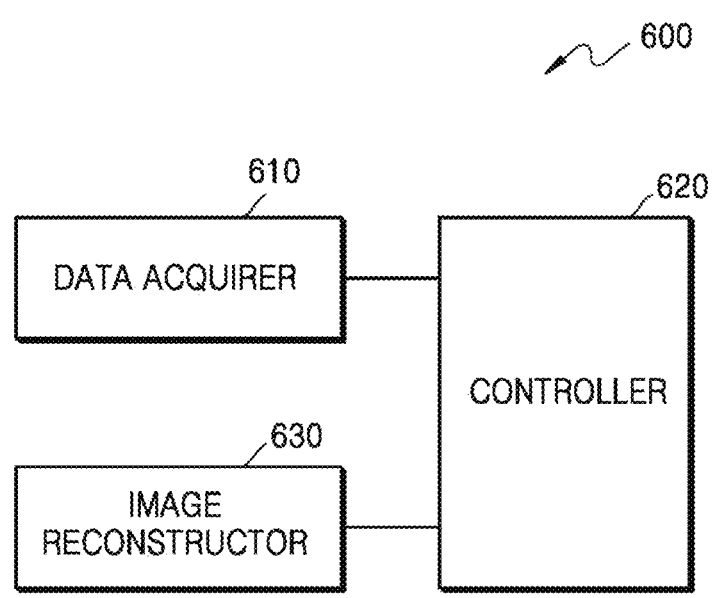
FIG. 6 is a block diagram of a configuration of a tomography apparatus according to an exemplary embodiment.

FIG. 6 is a block diagram of a configuration of a tomography apparatus 600 according to an exemplary embodiment.

Referring to FIG. 6, the tomography apparatus 600 according to the exemplary embodiment includes a data acquirer 610, a controller 620, and an image reconstructor 630.

The tomography apparatus 600 may be included in the CT system 100 or 500 described with reference to FIG. 3 or 6. Furthermore, the tomography apparatus 600 may be included in the medical apparatus 136 or the portable device 138 described with reference to FIG. 4 and be connected to the CT system 500 to be operated. In detail, the tomography apparatus 600 may be any medical imaging apparatuses adapted to reconstruct an image from data acquired using rays that have passed through an object. In other words, the tomography apparatus 600 may be any medical imaging apparatus reconstructing a tomography image from projection data acquired using rays that have passed through an object. For example, the tomography apparatus 600 may be a CT apparatus, an optical coherence tomography (OCT) apparatus, or a positron emission tomography (PET)-CT apparatus. Thus, a tomography image obtained by the tomography apparatus 600 may be a CT image, an OCT image, or a PET image. The following described figures show examples in which the tomography image is a CT image. Furthermore, if the tomography apparatus 600 is included in the CT system 100 described with reference to FIG. 3, the data acquirer 610 and the image reconstructor 630 shown in FIG. 6 may be included in the image processor 126 of FIG. 3. Furthermore, the data acquirer 610 may correspond to the DAS 116 and the data transmitter 120 of FIG. 3. The controller 620 and the image reconstructor 630 may respectively correspond to the controller 118 and the image processor 126 of FIG. 3.

The data acquirer 610 performs a tomography scan on an object to acquire tomography data with respect to the object. In detail, the object may include an organ. The object may include at least one of the heart, the abdomen, the uterus, the brain, a breast, and the liver. For example, the object may include the heart represented by a surface. In this case, the heart may include at least one tissue having different intensity values in a predetermined region.

The tomography data may be raw data. The raw data may be projection data obtained by projecting radiation onto the object, or may be a set of projection data called a sinogram. Furthermore, the raw data may be an image produced by performing filtered backprojection (FBP) on projection data or a sinogram. In detail, when the X-ray generator 106 emits an X-ray toward an object at a predetermined position, a viewpoint from which or direction in which the X-ray generator 106 faces the object is termed a view. Projection data means raw data acquired for each view, and a sinogram refers to raw data acquired by sequentially arranging a plurality of pieces of projection data.

According to an exemplary embodiment, a tomography image is reconstructed based on raw data acquired by using a plurality of X-ray generators (e.g., the first and second X-ray generators 510 and 520 of FIG. 5). An example in which a tomography image is reconstructed based on raw data acquired by using the first and second X-ray generators 510 and 520 that are two separate X-ray sources for generating X-rays having different energies, like in the CT system 500 described with reference to FIG. 5, will be described in detail below.

According to an exemplary embodiment, the data acquirer 610 may obtain a first image by using tomography data acquired as the first X-ray generator 510 for generating X-rays having a first energy rotates around the object over a first angular range. The data acquirer 610 may also obtain a second image by using tomography data acquired as the second X-ray generator 520 for generating X-rays having a second energy rotates around the object over a second angular range. Thus, the first and second images are respectively captured in first and second energy bands.

In this case, each of the first and second angular ranges refers to a partial angular range included in one period of angular range which is less than one rotation. According to an exemplary embodiment, the first and second angular ranges each have a value less than 180 degrees. The first and second images may be partial images. In detail, because the first and second images are respectively reconstructed only based on raw data acquired over certain angular ranges, the first and second images are not complete images showing the whole object but incomplete images showing parts of the object. An incomplete image showing a part of the object like the first and second images may be referred to as a partial image or partial angle image. The partial image may be reconstructed using a partial angle reconstruction (PAR) method.

A method of reconstructing a tomography image from raw data acquired as at least one X-ray generator rotates by an angle that is greater than or equal to 180 degrees and is less than 360 degrees is hereinafter referred to as a half reconstruction method. A method of reconstructing a tomography image from raw data acquired as the at least one X-ray generator rotates by 360 degrees is hereinafter referred to as a full reconstruction method. Furthermore, 'one period' is defined as a time period during which or an angle (or a phase) by which at least one X-ray generator rotates in order to acquire raw data needed for reconstructing a cross-sectional tomography image. Furthermore, 'one period of angular range' may be defined as an angular range over which at least one X-ray generator rotates in order to acquire raw data needed for reconstructing a cross-sectional tomography image. Furthermore, the 'one period of angular range' may be an interval of projection data necessary to reconstruct a cross-sectional tomography image, and in this case, may also be referred to as 'one period of angular range for projection data'.

For example, in half reconstruction performed by the CT system 100 including one X-ray generator 106, one period may be greater than or equal to 180°. For full reconstruction, one period may be 360 degrees. For example, for half reconstruction using a parallel beam obtained by performing a rebinning procedure, one period of angular range for projection data may be 180 degrees plus a fan angle'. For example, if a fan angle is about 60 degrees, one period of angular range for projection data in half reconstruction may be about 240 (180+60) degrees. For full reconstruction, one period of angular range may be about 360 degrees plus the fan angle, i.e., 420 (360+60) degrees.

According to an exemplary embodiment, the CT system 500 includes two X-ray generators, i.e., the first and second X-ray generators 510 and 520 for generating X-rays having different energies. In other words, the CT system 500 may include the first X-ray generator 510 for generating X-rays having a first energy and the second X-ray generator 520 for generating X-rays having a second energy.

According to an exemplary embodiment, the data acquirer 610 may acquire raw data corresponding to an angular range of 180 degrees plus an extra angle by using the first and second X-ray generators 510 and 520, and the extra angle may be in the range of about 30 degrees to about 70 degrees. The extra angle may vary depending on at least one of a shape of a beam used and specifications for a CT system and an X-ray generator.

As described above, the type of a tissue or body part of an object being clearly shown in an image may vary depending on an energy band of X-rays generated by each of the first and second X-ray generators 510 and 520. Thus, when a tomography image is reconstructed by using the first and second X-ray generators 510 and 520 that generate X-rays having different energies as described in the above exemplary embodiment, it is possible to obtain a tomography image clearly showing a particular tissue or body part that the user desires to analyze.

An operation of the tomography apparatus 600 according to the exemplary embodiment will now be described in more detail.

The data acquirer 610 may obtain a first image as a partial image by using tomography data acquired as the first X-ray generator 510 for generating X-rays having a first energy and the second X-ray generator 520 for generating X-rays for generating X-rays having a second energy respectively rotate around an object over first and second angular ranges. The data acquirer 610 may also obtain a second image as a partial image by using tomography data acquired as the first and second X-ray generators 510 and 520 respectively rotate around the object over the second angular range and a third angular range that is opposite to the first angular range. In this case, the first and second images are respectively captured in first and second energy bands.

In this case, each of the first through third angular ranges is a partial angular range included in one period of angular range which is less than one rotation. According to an exemplary embodiment, the first through third angular ranges may each have a value less than 180 degrees. Furthermore, the first and second images are partial images. In detail, because the first and second images are respectively reconstructed only based on raw data acquired over certain angular ranges, the first through fourth images are not complete images showing the whole object but incomplete images showing parts of the object.

The first and second X-ray generators 510 and 520 are used like in the CT system 500, and the first and second X-ray generators 510 and 520 that generate X-rays having different energies may respectively operate as different, independent sources. Thus, one period for half reconstruction is greater than or equal to 180 degrees while one period for full reconstruction is 360 degrees.

According to an exemplary embodiment, the data acquirer 610 may acquire two pieces of raw data corresponding to 180 degrees plus an extra angle by using the first and second X-ray generators 510 and 520. In this case, the extra angle may be in a range of about 30 degrees to about 70 degrees. The extra angle may vary depending on at least one of a shape of a beam used and specifications for a CT system and an X-ray generator.

In this case, when the first and second X-ray generators 510 and 520 are spaced at a 90-degree interval and rotate, one period for half reconstruction is greater than or equal to 90 degrees when a fan angle is taken into account, while one period for full reconstruction is greater than or equal to 270 degrees. Thus, raw data is acquired over one period of angular range as the first and second X-ray generators 510 and 520 respectively rotate around the object by 90 degrees plus a fan angle. In this case, the fan angle may be less than or equal to 90 degrees.

When a half reconstruction method is performed using one X-ray generator to reconstruct a tomography image, one period of angular range is greater than or equal to 180 degrees. On the other hand, when a tomography image is reconstructed by using two X-ray generators, i.e., the first and second X-ray generators 510 and 520 that rotate simultaneously, one period of angular range may be reduced to greater than or equal to 90 degrees. In other words, use of the first and second X-ray generators 510 and 520 reduces an angular range over which the first and second X-ray generators 510 and 520 rotate for reconstruction of a tomography image, thereby shortening the amount of time required to acquire data necessary for the reconstruction and accordingly increasing temporal resolution. Thus, according to an exemplary embodiment, more accurate tomography image may be reconstructed.

The controller 620 acquires motion information. In this case, the motion information may be information representing motion of a surface forming an object over time. Furthermore, the amount of motion may be generated due to motion of the object and may be at least one of differences between shapes, sizes, and positions of the object in the first and second images.

The image reconstructor 630 reconstructs a target image by using motion information. The image reconstructor 630 reconstructs a target image by correcting motion of an object based on motion information. In detail, the image reconstructor 630 may reconstruct a target image by warping an image showing the object, an image grid for imaging the object, or a voxel representing the object. In this case, warping means adjusting an object in an image to fit a predicted state of the object by changing a state of the object, e.g., by expanding and contracting the object, moving a position of the object, and/or changing a shape thereof.

According to an exemplary embodiment, the image reconstructor 630 may reconstruct a target image based on first and second reconstructed images that are respectively generated based on tomography data acquired during rotation of the first and second X-ray generators 510 and 520 by using the motion information. In this case, the image reconstructor 630 may reconstruct the target image by performing image registration between the first and second reconstructed images.

As described above, the type of a tissue or body part of an object being clearly shown in an image may vary depending on an energy band of X-rays generated by each of the first and second X-ray generators 510 and 520. Thus, when two tomography images corresponding to different energy bands are reconstructed by using the first and second X-ray generators 510 and 520 that generate X-rays having different energies and registered with each other, as described in the above exemplary embodiment, it is possible to obtain a tomography image clearly showing a particular tissue or body part that a user desires to analyze.

The target time point may be set by the image reconstructor 630 itself, or may be set to a predetermined value received from the user.

Furthermore, a tomography image may be reconstructed using various reconstruction methods. Examples of reconstruction methods used by the tomography apparatus 600 may include backprojection, FBP, an iterative method, etc.

Backprojection is a technique for reconstructing an image by adding up projection data acquired from a plurality of views back across an image plane. In detail, the backprojection method allows acquisition of an image similar to a real image by using the projection data acquired from the plurality of views. Furthermore, filtering may be performed additionally to remove artifacts in a reconstructed image and improve quality of the reconstructed image.

FBP is a technique that improves the performance of backprojection in order to eliminate artifacts or blurring that may occur during the backprojection. In the FBP method, raw data is filtered and then backprojected to reconstruct a tomography image.

The FBP method is the most commonly used in reconstruction of a tomography image. This method is easy to implement and is effective in terms of the amount of computation required for image reconstruction. The FBP method is a method of mathematically deriving an inverse transform from a Radon transform that is a process of acquiring a sinogram from a 2D image and allows simple expansion of a 2D image to a 3D image. In detail, according to the FBP method, projection data is filtered using a Shepp and Logan filter that is one type of high-pass filters and back-projected to reconstruct an image.

An example in which a tomography image is reconstructed using a FBP method will be described in detail below.

Although not shown in the drawings, according to an exemplary embodiment, the tomography apparatus 600 may further include a display, a user interface, a storage, and a communicator.

If an object moves like the heart, a time period or angle corresponding to one period, during which raw data is acquired, has to be minimized in order to reduce motion artifacts present in a reconstructed tomography image. Because a half reconstruction method may reduce motion artifacts more effectively than a full reconstruction method, an example in which a target image is reconstructed using a half reconstruction method will be described below.

Figure 7A:
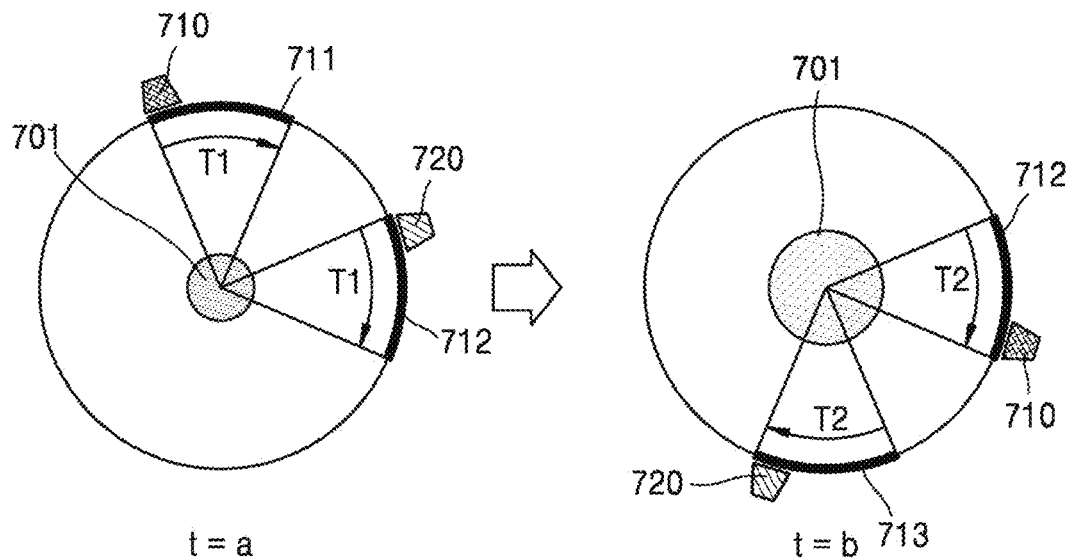
FIGS. 7A and 7B are diagrams for explaining an operation of a tomography apparatus according to an exemplary embodiment.
Figure 7B:
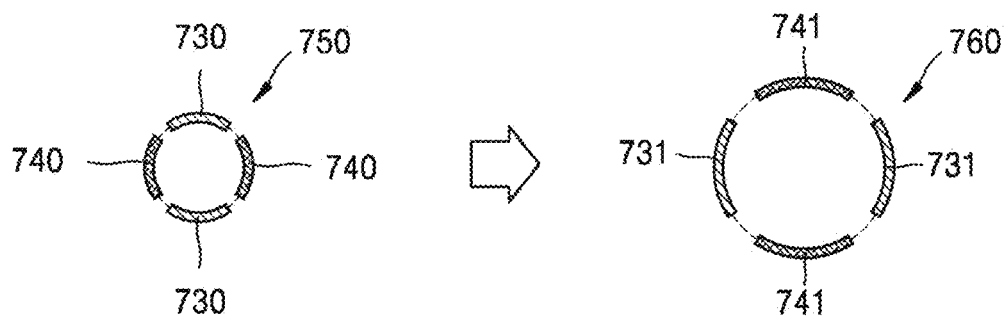

FIGS. 7A and 7B are diagrams for explaining an operation of the tomography apparatus 600 according to an exemplary embodiment.

Referring to FIGS. 7A and 7B, according to an exemplary embodiment, the tomography apparatus 600 may use tomography data acquired by using two X-ray generators for generating X-rays having different energies, i.e., first and second X-ray generators 710 and 720. Because the first and second X-ray generators 710 and 720 respectively correspond to the first and second X-ray generators 510 and 520 described with reference to FIG. 5, descriptions that are already provided with respect to FIG. 5 will be omitted here.

Referring to FIGS. 7A and 7B, a first image 750 is captured as the first X-ray generator 710 rotates over a first angular range 711 during a first time interval T1 while the second X-ray generator 720 simultaneously rotates over a second angular range 712. Furthermore, a second image 760 is captured as the first X-ray generator 710 rotates over the second angular range 712 during a second time interval T2 while the second X-ray generator 720 simultaneously rotates over a third angular range 713. The first and second images 750 and 760 are not complete images showing the whole object but incomplete images, i.e., partial images showing parts of the object.

Referring to FIG. 7A, scanning is performed on an object 701 during a time interval between time points t=a and t=b by using the first and second X-ray generators 710 and 720.

As described above, the type of a tissue or body part of an object being clearly shown in an image may vary depending on an energy band of X-rays generated by each of the first and second X-ray generators 510 and 520. Thus, when a tomography image is reconstructed by using the first and second X-ray generators 510 and 520 that generate X-rays having different energies as described in the above exemplary embodiment, it is possible to obtain a tomography image clearly showing a particular tissue or body part that a user desires to analyze.

Furthermore, when raw data is acquired over a certain angular range using the first and second X-ray generators 510 and 520, raw data acquisition time may be reduced by one-half, as compared to when raw data is acquired over the same angular range by using one X-ray generator. Faster raw data acquisition may shorten the total time when blurring occurs by one-half, and accordingly increase temporal resolution. High temporal resolution may reduce motion artifacts and allow more accurate reconstruction of a tomography image.

FIG. 7B is a schematic diagram illustrating partial images respectively captured during the first and second time intervals T1 and T2. During a tomography scan using X-rays, a portion of a surface being clearly imaged may vary according to a direction of an X-ray beam. In detail, a portion of the surface extending in a direction similar to a direction of an X-ray beam may be imaged more clearly than other portions thereof.

As seen on the first image 750, a surface 740 in a longitudinal direction may be clearly imaged because the first X-ray generator 710 emits X-rays in the longitudinal direction. In this case, because the second X-ray generator 720 emits X-rays in a transverse direction, a surface 730 in the transverse direction may also be clearly imaged. Furthermore, as seen on the second image 760, a surface 741 in the transverse direction may be clearly imaged because the first X-ray generator 710 emits X-rays in the transverse direction. In this case, because the second X-ray generator 720 emits X-rays in the longitudinal direction, a surface 731 in the longitudinal direction may also be clearly imaged.

In this way, use of the two X-ray generators (e.g., the first and second X-ray generators 710 and 720) allows a wider area of a surface to be clearly imaged as compared to use of one X-ray generator. In other words, surfaces in transverse and longitudinal directions may be clearly imaged during both the first and second time intervals T1 and T2, and accuracy of motion information representing motion of the object over time may be increased. Furthermore, by performing motion correction on an initial image based on highly accurate motion information, it is possible to reduce motion artifacts in a finally reconstructed target image.

In this case, images that can be obtained during the first and second time intervals T1 and T2 may be incomplete images reconstructed according to a PAR method.

Furthermore, by comparing the first image 750 acquired during the first time interval T1 with the second image 760 acquired during the second time interval T2, it is possible to estimate motion of the object 701 during the time interval between the time points t=a and t=b. The estimated motion of the object 701 may then be used for subsequent reconstruction of a tomography image.

In detail, the same surface of the object 701 is detected during a scan in the first and second time intervals T1 and T2. Thus, a PAR method may be used to reconstruct a tomography image based images acquired during the first and second time intervals T1 and T2.

According to an exemplary embodiment, the tomography apparatus 600 may reconstruct a tomography image by using the first and second X-ray generators 710 and 720 that rotate over a smaller angular range than one X-ray generator used in half reconstruction or full reconstruction, thus shortening raw data acquisition time. Faster data acquisition may increase temporal resolution and minimize motion artifacts. Furthermore, because surfaces in both the transverse and longitudinal directions may be clearly imaged for a view, the amount of motion of the object may be measured accurately, as described below with reference to FIG. 8.

Figure 8:
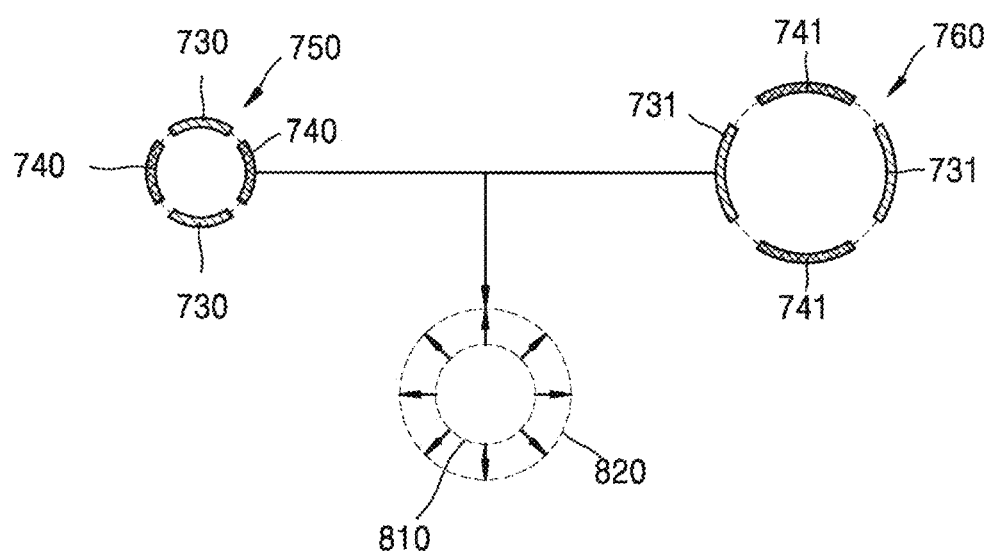
FIG. 8 is a diagram for explaining about movement of an object.

FIG. 8 is a diagram for explaining motion of an object.

FIG. 8 illustrates motion of the object during the operation of the tomography apparatus 600 Illustrated in FIGS. 7A and 7B. In FIGS. 7A and 7B and 8, like reference numerals refer to like elements.

As apparent from FIG. 8, a size of the object 701 in the second time interval T2 is increased compared to that of the object 701 in the first time interval T1. In other words, a size of the object 701 is increased from a first size 810 to a second size 820 between the first and second time intervals T1 and T2. The object 701 represented as a surface in a 3D tomography image may be depicted as edges (e.g., 730, 731, 740, and 741) in a 2D tomography image shown in FIG. 8.

By comparing the first image 750 acquired during the first time interval T1 with the second image 760 acquired during the second time interval T2, motion of the object 701 during the time interval between the time points t=a and t=b may be estimated. In detail, by comparing differences between corresponding edges (e.g., by comparing a difference between the edges 730 and 741 and a difference between the edges 731 and 740) respectively included in the first and second images 750 and 760 and representing the same surface of the object 701, the extent of motion of the object 701 may be determined.

Furthermore, a 3D tomography image may be reconstructed as first and second images, and then the first and second images may be used to determine the amount of motion of the object. When a 3D tomography image is reconstructed as first and second images, the amount of motion of an object that occur during a time interval between time points t=a and t=b may be determined by comparing differences between corresponding edges respectively included in the first and second images 750 and 760 and representing the same surface of an object.

Figure 9A:
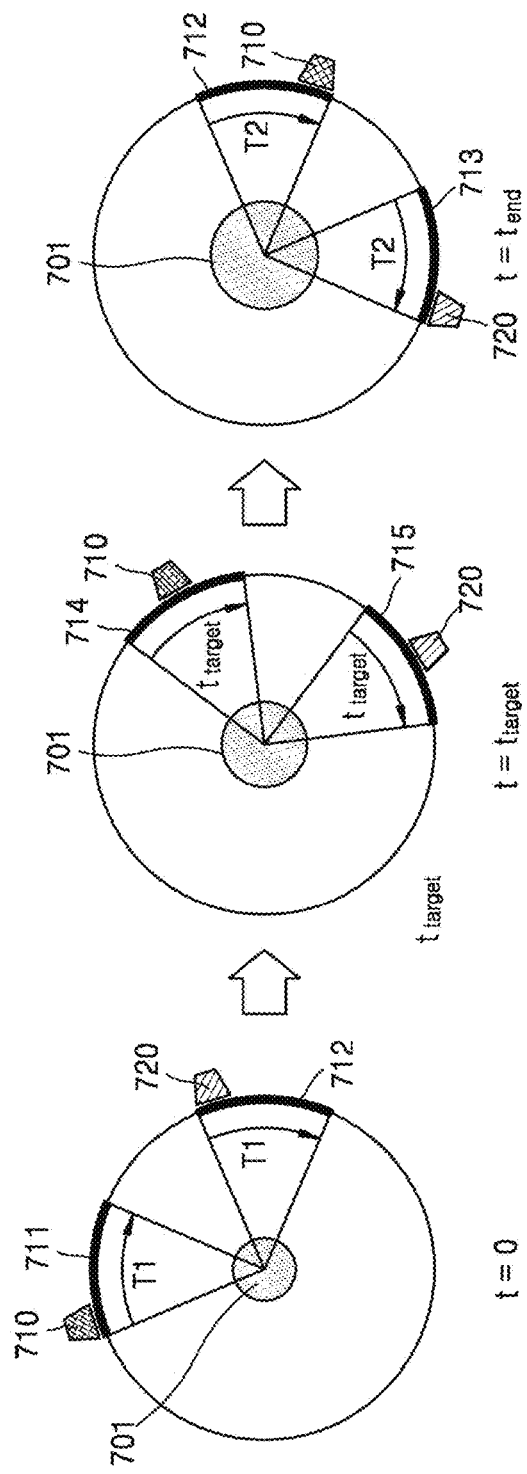
FIGS. 9A and 9B are other diagrams for explaining about an operation of a tomography apparatus according to an exemplary embodiment.
Figure 9B:
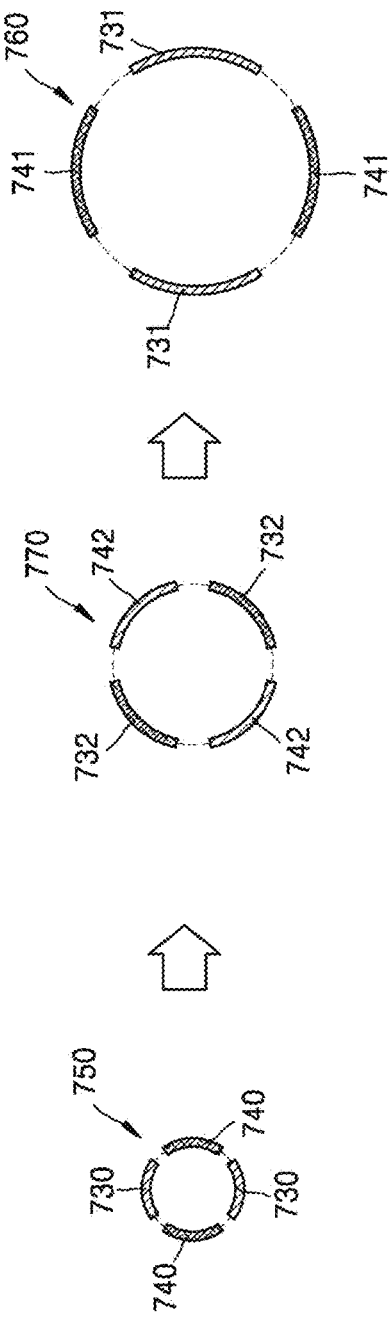

FIGS. 9A and 9B are other diagrams for explaining an operation of the tomography apparatus 600 according to an exemplary embodiment. In FIGS. 7A and 7B and 9A and 9B, like reference numerals refer to like elements.

FIGS. 9A and 9B illustrate a process whereby the tomography apparatus 600 including the first and second X-ray generators 710 and 720 disposed at 90-degree intervals performs a tomography scan for reconstructing an image.

Referring to FIG. 9A, raw data is acquired as the first and second X-ray generators 710 and 720 rotate 90 degrees around the object 701 during a time interval between time points t=0 and t=$t_{end}$ and emits X-rays. While FIG. 9 shows for convenience that the first and second X-ray generators 710 and 720 rotate 90 degrees, the first and second X-ray generators 710 and 720 have to rotate by 90 degrees plus an extra angle during an actual scan. The acquired raw data is used to reconstruct a tomography image. In detail, a plurality of pieces of filtered projection data are acquired as the first and second X-ray generators 710 and 720 emit X-rays at a plurality of points (a plurality of views) during rotation thereof. The plurality of pieces of filtered projection data are then accumulated and backprojected to reconstruct a tomography image. In other words, an image of an object may be obtained by a backprojection process whereby filtered projection data is applied to image pixels.

However, a mismatch in surface information between pieces of filtered projection data respectively acquired at a plurality of views occurs due to motion of an object. Thus, if a plurality of pieces of filtered projection data acquired during one period of angular range are accumulated, a surface of an object may not be clearly represented and appear blurred. Thus, it is possible to obtain a clearer image by reconstructing a tomography image after estimating motion of the object and performing motion correction on an initial image based on the estimated motion of the object.

According to an exemplary embodiment, the first image 750 is acquired as the first and second X-ray generators 710 and 720 simultaneously rotate around the object 701 being scanned over the first and second angular ranges 711 and 712, respectively, during the first time interval T1. Furthermore, the second image 760 is acquired as the first and second X-ray generators 710 and 720 simultaneously rotate around the object 701 being scanned over the second and third angular ranges 712 and 713, respectively, during the second time interval T2. In this case, because the first and second images 750 and 760 are reconstructed only based on raw data acquired over certain angular ranges, they are not complete images showing the whole object but incomplete images, i.e., partial images, showing parts of the object.

In PAR, a portion being clearly shown in a reconstructed image may vary according to a view angle at which an X-ray is emitted. In detail, surfaces (undergo more or less sampling according to a view angle. According to an exemplary embodiment, because the tomography apparatus 600 includes the first and second X-ray generators 710 and 720 disposed at a 90-degree interval, surfaces in both the transverse and longitudinal directions may be imaged clearly. Thus, almost all surfaces may be imaged clearly. Furthermore, if a target time point is set to a mid time point between start and end time points, even edges of the surfaces in the transverse and longitudinal directions may be clearly imaged.

FIG. 9B illustrates surfaces of the object 701 scanned during rotation of the first and second X-ray generators 710 and 720. The first and second X-ray generators 710 and 720 are disposed at a 90-degree interval so that almost all the surfaces of the object 710 may be clearly imaged.

According to an exemplary embodiment, by comparing the first image 750 acquired during the first time interval T1 with the second image 760 acquired during the second time interval T2, it is possible to estimate motion of the object 701 during the time interval between the time points t=0 and t=$t_{end}$. In detail, by comparing differences between corresponding edges (e.g., by comparing a difference between the edges 730 and 741 and a difference between the edges 731 and 740) respectively included in the first and second images 750 and 760 and representing the same surface of the object 701, the extent of motion of the object 701 may be determined. A target image may be obtained by correcting motion of the object 701 at target time point $t_{target}$ between t=0 and t=$t_{end}$ based on the estimated motion of the object 701.

In the exemplary embodiments shown in FIGS. 7A, 7B, 8, 9A, and 9B, it has been described that the first image 750 includes all surfaces of the object 710 scanned by rotation of the first and second X-ray generators 710 and 720 during the first time interval T1. Unlike in the exemplary embodiments, a first image may be an image of a surface of the object 701 captured by rotation of the first X-ray generator 710 during the first time interval T1, and a second image may be an image of a surface of the object 701 captured by rotation of the second X-ray generator 720 during the second time interval T2. In this case, a narrower surface may be imaged than in the exemplary embodiments shown in FIGS. 7A, 7B, 8, 9A, and 9B. However, the amount of data that needs to be processed may be reduced and thus, data processing time may be shortened.

Figure 10:
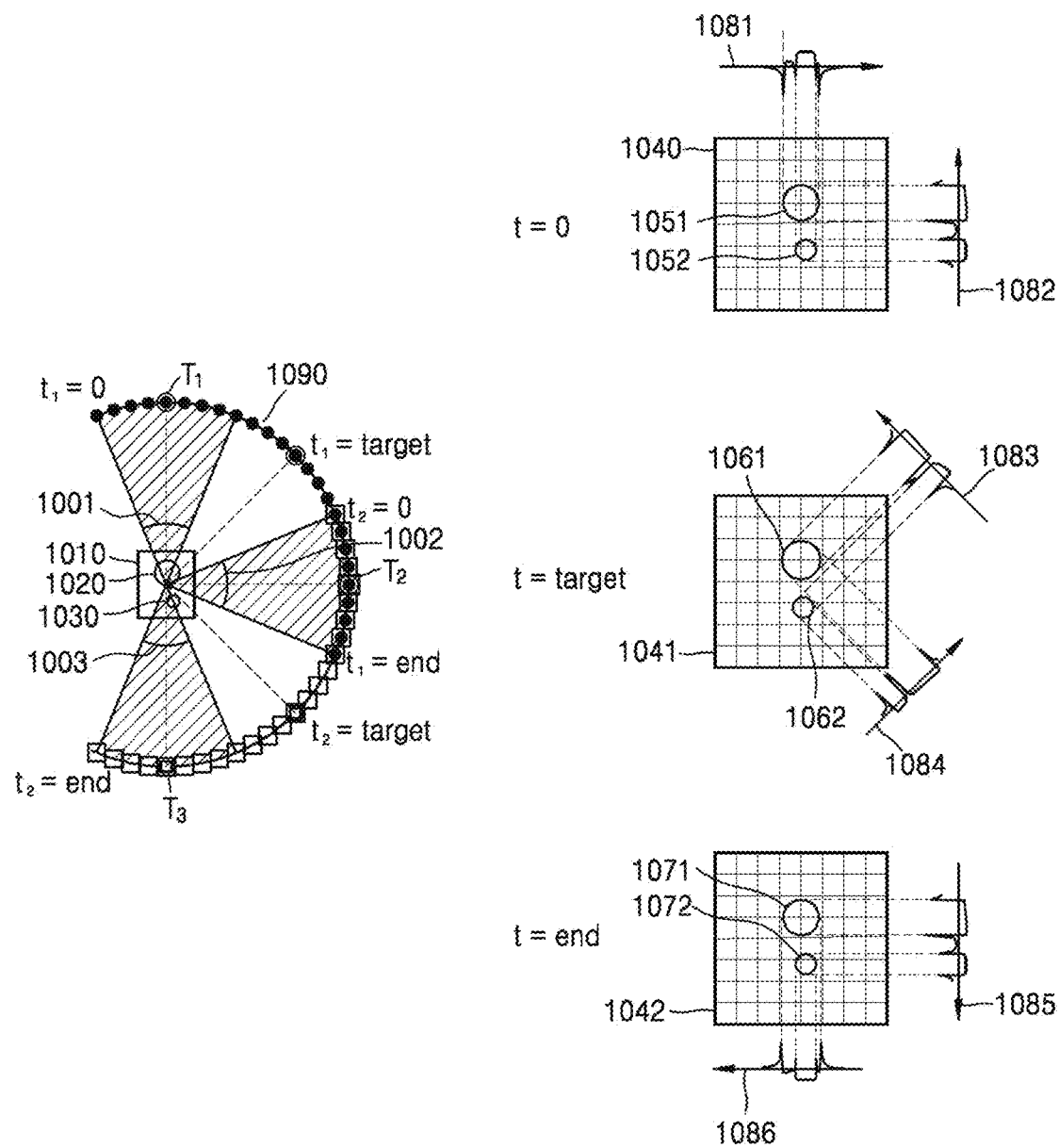
FIG. 10 is a diagram for explaining about a method of reconstructing a tomography image, according to an exemplary embodiment.

FIG. 10 is a diagram for explaining a method of reconstructing a tomography image, according to an exemplary embodiment.

In particular, FIG. 10 relates to a method of reconstructing a tomography image based on data acquired while scanning an object 1010 as the first and second X-ray generators 710 and 720 rotate. Referring to FIG. 10, projection data is acquired as the first and second X-ray generators 710 and 720 emit X-rays toward the object 1010 respectively at a plurality of positions having a predetermined angle interval as they move along a circular source trajectory 1090. Then, filtered projection data is acquired by filtering the projection data.

A plurality of circular points along the circular source trajectory 1090 represent positions where the first X-ray generator 710 is located to emit X-rays. Furthermore, a plurality of squares represent positions where the second X-ray generator 720 is located to emit X-rays. For example, the first and second X-ray generators 710 and 720 may emit X-rays toward the object 1010 by moving at predetermined intervals such as every 0.5-degree, 1-degree, or 3-degree intervals. The first X-ray generator 710 rotates starting from a first position T1 and ending at a second position T2. Furthermore, the second X-ray generator 720 rotates starting from the second position T2 and ending at a third position T3. According to an exemplary embodiment, although an extra angle has to be further taken into account during rotation of the first and second X-ray generators 710 and 720, for convenience of explanation, positions where the first and second X-ray generators 710 and 720 rotate are assumed herein to be the first through third positions T1 through T3. If the first position T1 is 0 degree, the third position T3 may correspond to 180 degrees. In this case, when the first and second X-ray generators 710 and 720 are coupled to the same rotating frame 104 for rotation thereof, the first and second X-ray generators 710 and 720 have the same angular velocity. In other words, because the first and second X-ray generators 710 and 720 rotate over different angular ranges, the angular ranges respectively have the same start points ($t_1=0$ and $t_2=0$) and the same end points ($t_1$=end and $t_2$=end).

In detail, when the first X-ray generator 710 emits X-rays toward the object 1010 while rotating over a first angular range 1001, a signal 1081 is acquired which is the same as a signal acquired as an X-ray emitted from the first position T1 toward the object 1010 passes through the object 1010. Furthermore, when the second X-ray generator 720 emits X-rays toward the object 1010 while rotating over a second angular range 1002 during the same time interval, a signal 1082 is acquired which is the same as a signal acquired as an X-ray emitted from the second position T2 toward the object 1010 passes through the object 1010. The acquired signals 1081 and 1082 may each have varying values on a surface of the object 1010 due to a difference in the rate of penetration of the X-rays through materials. In detail, values of the signal 1081 or 1082 may vary on surfaces that are parallel to directions that X-rays are emitted.

Furthermore, when the first X-ray generator 710 emits X-rays toward the object 1010 while rotating over a first target angular range, a signal 1083 is acquired which is the same as a signal acquired as an X-ray emitted toward the object 1010 at a first target time point $t_1$=target passes through the object 1010. Furthermore, when the second X-ray generator 720 emits X-rays toward the object 1010 while rotating over a second target angular range during the same time interval, a signal 1084 is acquired which is the same as a signal acquired as an X-ray emitted toward the object 1010 at a second target time point t2=target passes through the object 1010. The acquired signals 1083 and 1084 may each have varying values on a surface of the object 1010 that is parallel to a direction in which an X-ray is emitted.

Furthermore, when the first X-ray generator 710 emits X-rays toward the object 1010 while rotating over the second angular range 1002, a signal 1085 is acquired which is the same as a signal acquired as an X-ray emitted from the second position T2 toward the object 1010 passes through the object 1010. Furthermore, when the second X-ray generator 720 emits X-rays toward the object 1010 while rotating over a third angular range 1003 during the same time interval, a signal 1086 is acquired which is the same as a signal acquired as an X-ray emitted from the third position T3 toward the object 1010 passes through the object 1010. The acquired signals 1085 and 1086 may each have varying values on a surface of the object 1010 that is parallel to a direction that an X-ray is emitted.

Because each of the signals 1081 through 1086 includes information about a surface that is parallel to a direction in which an X-ray is emitted, an image is obtained by performing FBP on each of the signals 1081 through 1086. The obtained image contributes to imaging the surface that is parallel to a direction in which an X-ray is emitted. In other words, projection data acquired at each view contributes to imaging a surface of the object corresponding to the view. This method may be explained using a Fourier slice theorem that describes the relationship between a value of projection data acquired by projecting a parallel beam to the object 1010 and a frequency component of an image. In this case, a 'view' corresponds to a direction, a position, and/or a rotational angle where the first and second X-ray generators 710 and 720 emit X-rays toward the object 1010.

As described above, the type of a tissue or body part of an object being clearly shown in an image may vary depending on an energy band of X-rays generated by each of the first and second X-ray generators 510 and 520. These characteristics will be described again below with reference to FIG. 14.

Furthermore, the DAS 116 described with reference to FIG. 3 may acquire a signal (e.g., the signal 1081). The image processor 126 may process the acquired signal 1081 to generate filtered projection data and then backproject the filtered projection data to obtain an image.

In detail, when a plurality of pieces of filtered projection data are acquired while the first and second X-ray generators 710 and 720 emit X-rays at a plurality of points (a plurality of views) during rotation thereof, the plurality of pieces of filtered projection data are accumulated and backprojected to reconstruct a tomography image. In other words, an image representing the object 1010 may be obtained by a back-projection process whereby the pieces of filtered projection data are applied to image pixels.

However, a mismatch in surface information between pieces of filtered projection data respectively acquired at a plurality of views occurs due to motion of an object. Thus, if a plurality of pieces of filtered projection data acquired during one period of angular range are accumulated, a surface of an object may not be clearly represented and appear blurred. Thus, it is possible to obtain a clearer image by reconstructing a tomography image after estimating motion of the object and performing motion correction on an initial image based on the estimated motion of the object. A process of acquiring motion information based on the obtained image and reconstructing a target image will now be described with reference to FIGS. 10 and 11A and 11B.

Figure 11A:
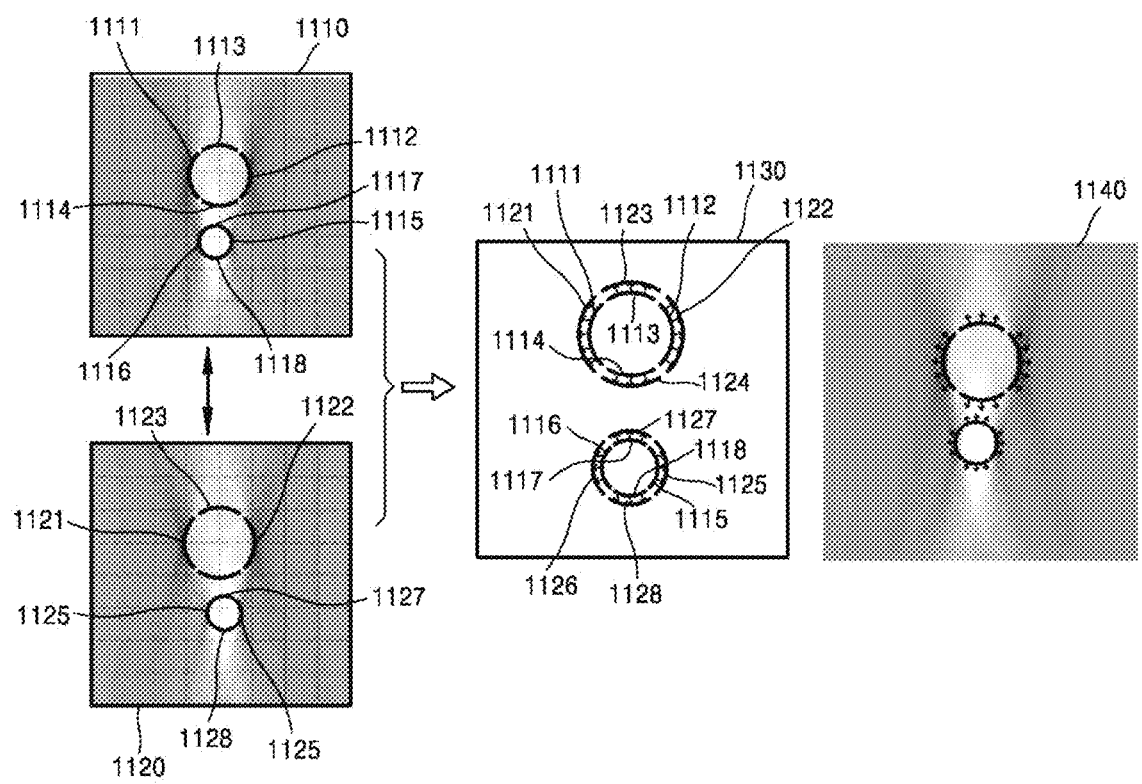
FIGS. 11A and 11B are another diagram for explaining about a method of reconstructing a tomography image according to an exemplary embodiment.

Referring to FIGS. 10 and 11A, a first image 1110 is obtained by using pieces of projection data corresponding to the first and second angular ranges 1001 and 1002 and respectively acquired as the first and second X-ray generators 710 and 720 rotate around the object 1010. Surfaces 1111 through 1114 forming a first entity 1020 and surfaces 1115 through 1118 forming a second entity 1030 are shown in the first image 1110. Furthermore, a second image 1120 is obtained by using pieces of projection data corresponding to the second and third angular ranges 1002 and 1003 and respectively acquired as the first and second X-ray generators 710 and 720 rotate around the object 1010. Surfaces 1121 through 1124 forming the first entity 1020 and surfaces 1125 through 1128 forming the second entity 1030 are shown in the second image 1120. In other words, pieces of projection data acquired at each view or over a predetermined angular range included in one period of angular range contribute to imaging different surfaces or regions of the object 1010. According to an exemplary embodiment, by acquiring projection data via the first and second X-ray generators 710 and 720, an area that can be imaged at one time may be increased. In this case, because the first and second images 1110 and 1120 are reconstructed only from raw data acquired over certain angular ranges, the first and second images 1110 and 1120 may be complete images showing the whole object 1010 but incomplete images, i.e., partial images showing parts of the object 1010.

Furthermore, because the first and second images 1110 and 1120 are reconstructed from projection data acquired in a short time by using the first and second X-ray generators 710 and 720, the total time when blurring occurs is shortened, and accordingly a high temporal resolution is provided. Thus, the first and second images 1110 and 1120 may have minimized motion artifacts.

Because surfaces of the same part of the object 1010 are shown in the first and second images 1110 and 1120, the data acquirer 610 acquires a motion vector field (MVF) 1140 representing motion of the object 1010 by comparing the first image 1110 with the second image 1120 as illustrated in an image 1130. The MVF 1140 includes vectors, each vector representing a direction of movement of a surface of the same part of the object 1010 and extent (a magnitude) of movement thereof. Thus, motion information representing the amounts of motion of the object 1010 over time between time points $t_1=0$ and $t_1=\text{end}$ and between time points $t_2=0$ and $t_2=\text{end}$ may be acquired based on the MVF 1140. The extent of motion of the object 1010 at target time points $t_1=\text{target}$ and $t_2=\text{target}$ may be predicted based on the motion information. Alternatively, a state of the object 1010 including at least one of a size, a shape, and a position of the object 1010 at the target time point $t_1=\text{target}$ ($t_2=\text{target}$) may be predicted using the motion information. In this case, as described above, when the first and second X-ray generators 710 and 720 are coupled to the same rotating frame 104 for rotation thereof, the first and second X-ray generators 710 and 720 have the same angular velocity. In other words, because the first and second X-ray generators 710 and 720 rotate over different angular ranges, the angular ranges respectively have the same start points ($t_1=0$ and $t_2=0$) and the same end points ($t_1=\text{end}$ and $t_2=\text{end}$).

Before reconstructing a target image, by using the motion information, the image reconstructor 630 may perform motion correction on a surface or region of the object 1010 being imaged using pieces of projection data acquired at time points other than the target time points $t_1=\text{target}$ and $t_2=\text{target}$ and not on a surface or region of the object 1010 being imaged using projection data acquired at the target time points $t_1=\text{target}$ and $t_2=\text{target}$. In detail, a total amount by which the object 1010 has moved between time points $t_1=0$ and $t_1=\text{end}$ and between time points $t_2=0$ and $t_2=\text{end}$ is defined as a total amount of motion W, and the total amount of motion $W=1$. In this case, the amount of motion W may correspond to differences between the amounts of motion W1 at the start time point $t1=0$ and the target time point $t1=\text{target}$ and between the amounts of motion W2 at the start time point $t2=0$ and the target time point $t2=\text{target}$. In this case, a corrected partial image may be generated by performing motion correction on a partial image based on the amount of motion that has occurred during an interval between the start time point $t_1=0$ ($t_2=0$) and the target time point $t_1=\text{target}$ ($t_2=\text{target}$) against the total amount of motion W. Because corrected partial images accurately reflect states of motion of the object 1010 at the target time points $t_1=\text{target}$ and $t_2=\text{target}$, the target image reconstructed using the corrected partial images may have minimized motion artifacts.

Figure 11B:
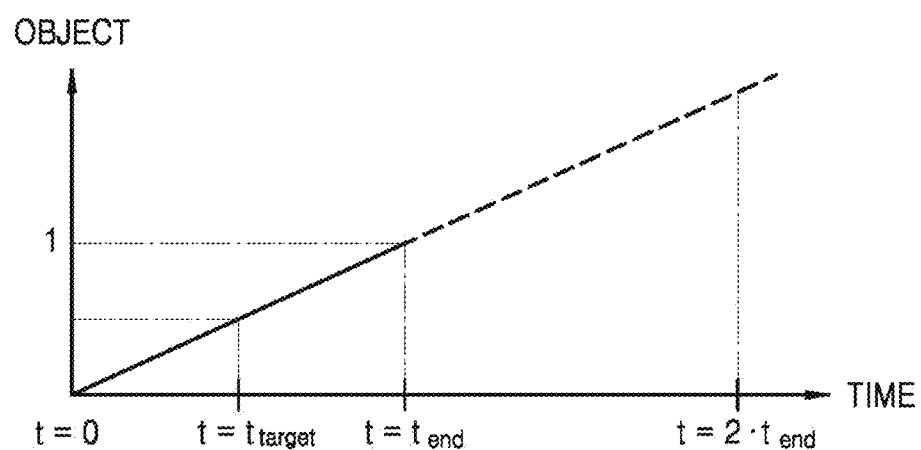

Referring to FIG. 11B, an x-axis and a y-axis respectively represent time and motion of an object. If motion of the object is 0 at $t=0$, motion of the object is assumed to be 1 at $t=t_{end}$ when rotation ends. Furthermore, if $t=t_{end}$ is the time required for two X-ray generators to rotate over one period of angular range, the time required for one X-ray generator to rotate over the same period of angular range may be about $2 \times t_{end}$. In other words, use of the two X-ray generators reduces an angular range over which the two X-ray generators have to rotate for reconstruction of a tomography image.

Thus, the time needed to acquire data for reconstruction of a tomography image may be reduced, and temporal resolution may be increased. According to an exemplary embodiment, it is therefore possible to reconstruct a more accurate tomography image.

Figure 12A:
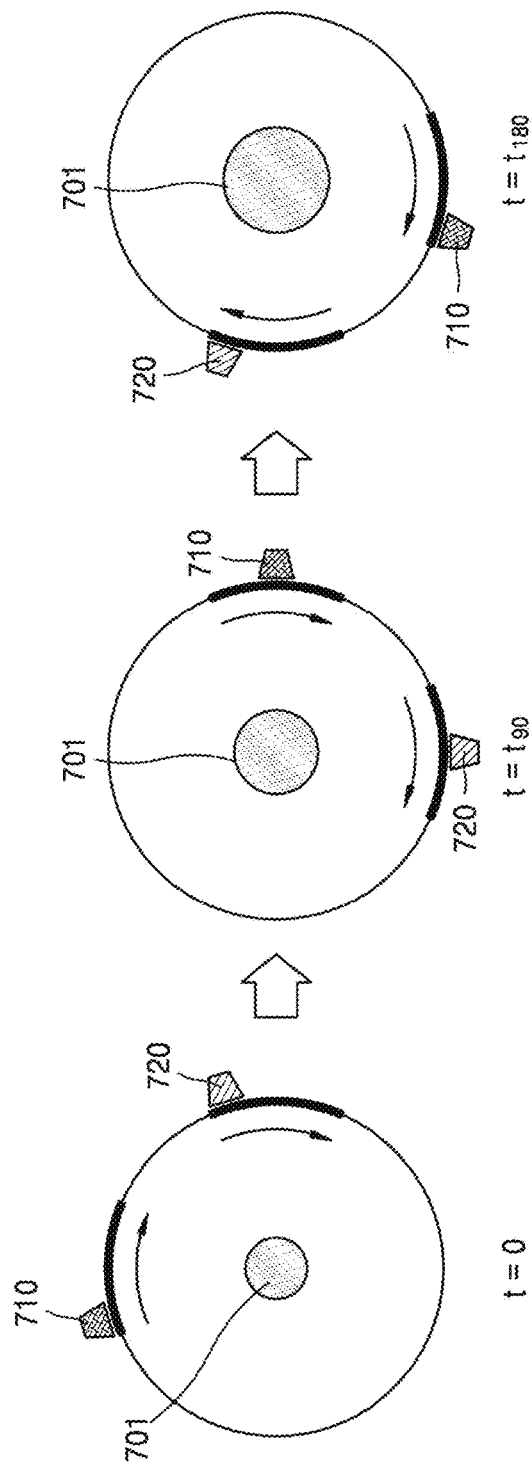
FIGS. 12A and 12B are other diagrams for explaining about an operation of a tomography apparatus according to an exemplary embodiment.
Figure 12B:
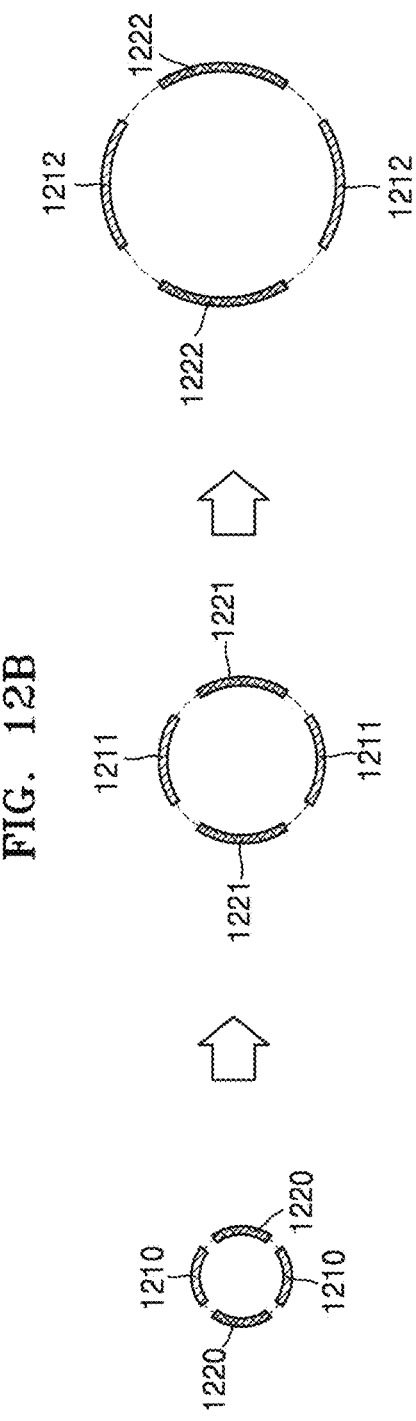
Figure 13:
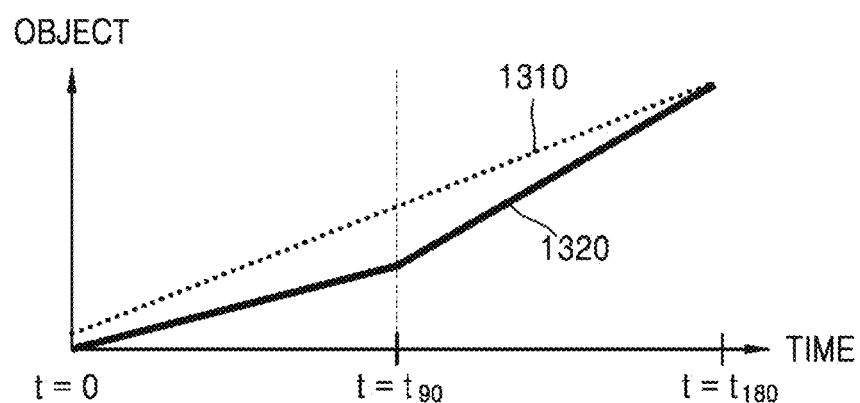
FIG. 13 is a graph of the amount of motion of an object with respect to time.

FIGS. 12A and 12B are other diagrams for explaining an operation of the tomography apparatus 600 according to an exemplary embodiment, and FIG. 13 is a graph of the amount of motion of an object with respect to time. In FIGS. 7A, 7B, and 12, like reference numerals refer to like elements.

Referring to FIGS. 12A and 12B, the tomography apparatus 600 may use tomography data acquired by using the first and second X-ray generators 710 and 720. In FIG. 12A, scanning is performed on the object 701 during a time interval from $t=0$ to $t=t_{180}$ by using the first and second X-ray generators 710 and 720.

FIG. 12B illustrates motions of the object 701 at time points $t=0$, $t=t_{90}$, and $t=t_{180}$ during a tomography scan. As seen on FIG. 12B, motion of the object 701 occurs to a relatively small extent during an interval between $t=0$ and $t=t_{90}$, while motion to the object 701 occurs to a relatively large extent during an interval between $t=t_{90}$ and $t=t_{180}$. FIG. 13 is a graph of the amount of motion of the object 701 with respect to time.

Referring to FIG. 13, an x-axis and a y-axis respectively represent time and motion of an object. If motion of the object is 0 at $t=0$, motion of the object is assumed to be 1 at $t=t_{180}$ when rotation ends. When data is acquired using only one X-ray generator (e.g., the second X-ray generator 720), because motion information is generated based on partial images acquired at $t=0$ and $t=t_{180}$, the motion information cannot reflect a change of motion that occurs between $t=0$ and $t=t_{90}$ (e.g., at $t=t_{90}$). In other words, the amount of motion between $t=0$ and $t=t_{180}$ may only be estimated as indicated by a dotted line 1310.

On the other hand, when data is acquired using two X-ray generators (e.g., the first and second X-ray generators 710 and 720), because motion information may be generated based on partial images acquired at $t=0$ and $t=t_{90}$ and partial images acquired at $t=t_{90}$ and $t=t_{180}$, more accurate motion information may be acquired by reflecting even a change of motion that occurs between $t=0$ and $t=t_{90}$ (e.g., at $t=t_{90}$). In other words, the amount of motion between $t=0$ and $t=t_{180}$ may be estimated as indicated by a solid line 1320.

In this way, when a tomography scan is performed by using two X-ray generators (e.g., the first and second X-ray generators 710 and 720) during a time interval having the same length as when using one X-ray generator, more accurate motion information may be acquired, and a more accurate reconstructed image may be obtained.

FIGS. 14A and 14B are diagrams for explaining about a process of reconstructing a tomography image according to an exemplary embodiment.

FIGS. 14A and 14B respectively illustrate raw data respectively acquired by using the first and second X-ray generators 710 and 720. In other words, images 1411, 1421, 1431, 1441, 1451, and 1461 may be obtained by performing FBP on the signals 1471 through 1476, respectively.

Referring to FIGS. 10 and 11A, the object 1010 may include first and second entities 1020 and 1030. In this case, energy bands of X-rays that can image the first and second entities 1020 and 1030 clearly are different from each other.

Referring to FIG. 14A, in the images 1411, 1431, and 1451 obtained by using the first X-ray generator 710, first entities 1412, 1432, and 1452 are shown more clearly than second entities 1413, 1433, and 1453. On the other hand, referring to FIG. 14B, in the images 1421, 1441, and 1461 obtained by the second X-ray generator 720, second entities 1423, 1443, and 1463 are shown more clearly than first entities 1422, 1442, and 1462. In other words, X-rays generated by the first X-ray generator 710 have an energy band that can image the first entities 1412, 1432, and 1452 more clearly than the second entities 1413, 1433, and 1453, while X-rays generated by the second X-ray generator 720 have an energy band that can image the second entities 1423, 1443, 1463 more clearly than the first entities 1422, 1442, and 1462. In this way, images are obtained by using the first and second X-ray generators 710 and 720 for generating X-rays having different energy bands, and a target image is reconstructed based on the obtained images, thereby allowing reconstruction of a more accurate tomography image.

Figure 15:
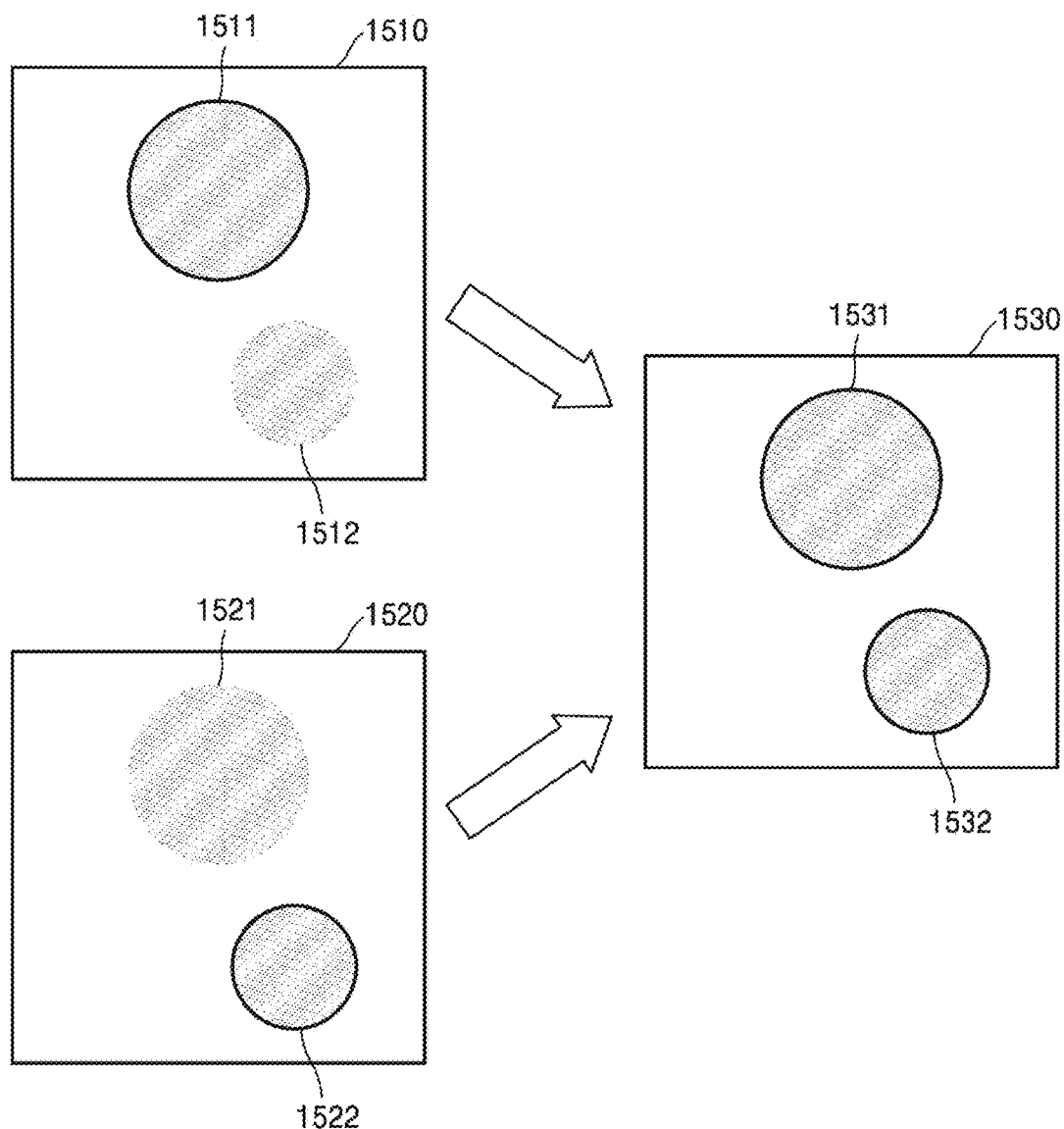
FIG. 15 is another diagram for explaining about a process of reconstructing a tomography image according to an exemplary embodiment.

FIG. 15 is another diagram for explaining about a process of reconstructing a tomography image according to an exemplary embodiment.

FIG. 15 illustrates a process of reconstructing a target image 1530 based on images 1510 and 1520 respectively obtained by using the first and second X-ray generators 710 and 720.

In the image 1510 obtained by the first X-ray generator 710, a first entity 1511 appears clearer than a second entity 1512. In the image 1520 obtained by the second X-ray generator 720, a second entity 1522 appears clearer than a first entity 1521. According to an exemplary embodiment, the image reconstructor 630 of the tomography apparatus 600 may reconstruct the target image 1530 based on the images 1510 and 1520 respectively obtained by the first and second X-ray generators 710 and 720. In this case, by selecting and registering portions clearly shown in the images 1510 and 1520 respectively obtained by the first and second X-ray generators 710 and 720, a more accurate tomography image may be reconstructed.

Figure 16:
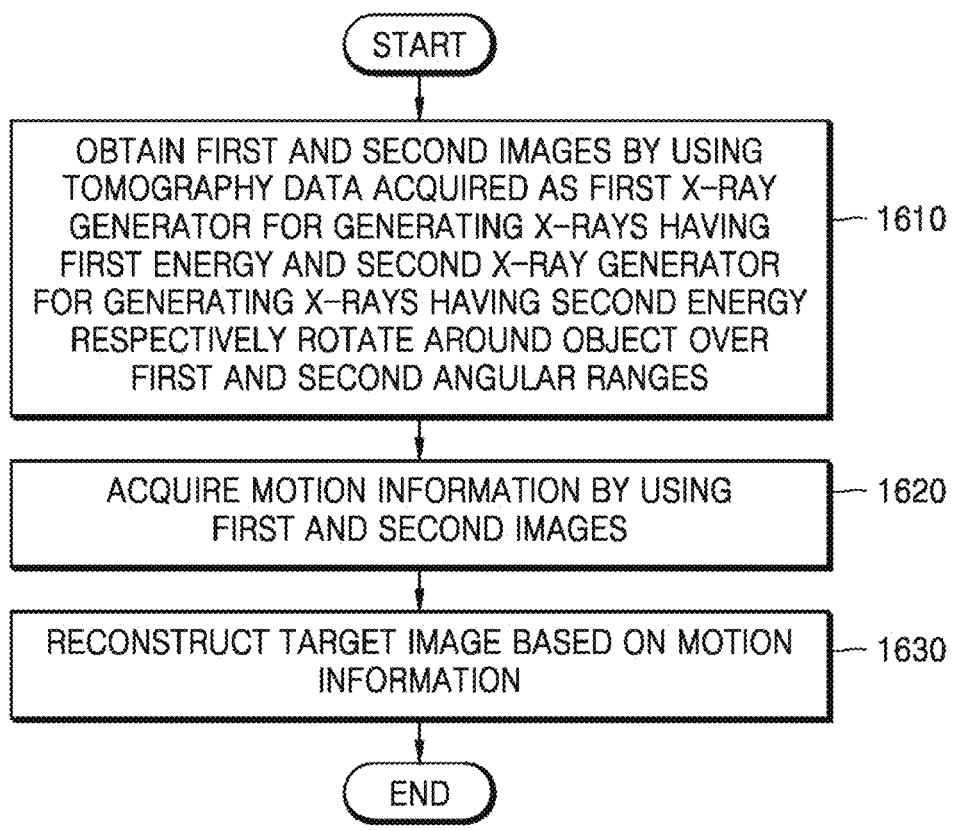
FIG. 16 is a flowchart of a method of reconstructing a tomography image according to an exemplary embodiment.

FIG. 16 is a flowchart of a method of reconstructing a tomography image according to an exemplary embodiment.

Referring to FIG. 16, a first image is obtained by using tomography data acquired as a first X-ray generator for generating X-rays having a first energy rotates around an object over a first angular range, and a second image is obtained by using tomography data acquired as a second X-ray generator for generating X-rays having a second energy rotates around the object over a second angular range (operation 1610). According to an exemplary embodiment, the first and second images may be partial images, and the first and second angular ranges may be opposite to each other. Furthermore, the first and second angular ranges may be less than 180 degrees, respectively. In addition, two pieces of tomography data corresponding to an angular range of 180 degrees plus an extra angle may be acquired by respectively using the first and second X-ray generators, and the extra angle may be in a range of about 30 degrees to about 70 degrees. Operation 1610 may be performed by the data acquirer 610 of the tomography apparatus 600.

Thereafter, motion information representing the amount of motion of the object over time is acquired by using the first and second images (operation 1620). According to an exemplary embodiment, the motion information may represent the amount of motion of a surface forming the object. Operation 1620 may be performed by the controller 620 of the tomography apparatus 600.

Lastly, a target image showing the object at a target time point is reconstructed by using the motion information (operation 1630). According to an exemplary embodiment, the target image may be reconstructed based on first and second reconstructed images which are respectively generated based on tomography data acquired during rotation of the first and second X-ray generators by using the motion information. Then, the target image may be reconstructed by performing image registration between the first and second reconstructed images. Operation 1630 may be performed by the image reconstructor 630 of the tomography apparatus 600 data acquirer.

Figure 17:
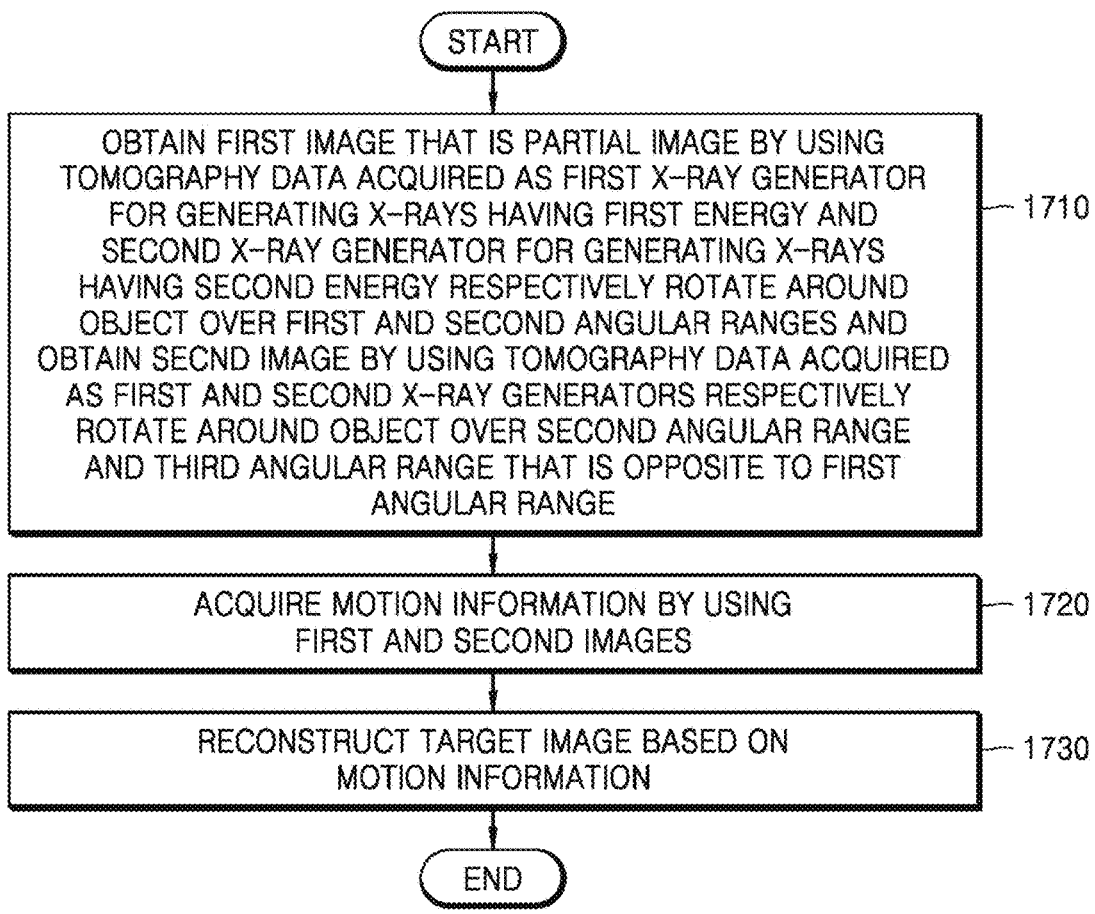
FIG. 17 is a flowchart of a method of reconstructing a tomography image according to another exemplary embodiment.

FIG. 17 is a flowchart of a method of reconstructing a tomography image according to another exemplary embodiment.

Referring to FIG. 17, first, a first image that is a partial image is obtained by using tomography data acquired as a first X-ray generator for generating X-rays having a first energy and a second X-ray generator for generating X-rays having a second energy respectively rotate around an object over a first angular range and a second angular range, and a second image that is a partial image is obtained by using tomography data acquired as the first and second X-ray generators respectively rotate around the object over the second angular range and a third angular range that is opposite to the first angular range (operation 1710). According to an exemplary embodiment, each of the first through third angular ranges may be less than 180 degrees. Furthermore, the first and second X-ray generators may be spaced apart by a 90 degree interval. Furthermore, the tomography data may be acquired as the first and second X-ray generators respectively rotate around the object by 90 degrees plus an extra angle, and the extra angle may be less than or equal to 90 degrees. In addition, two pieces of tomography data corresponding to an angular range of 180 degrees plus an extra angle may be acquired by respectively using the first and second X-ray generators, and the extra angle may be in the range of about 30 degrees to about 70 degrees. Operation 1710 may be performed by the data acquirer 610 of the tomography apparatus 600.

Thereafter, motion information representing the amount of motion of the object over time is acquired by using the first and second images (operation 1720). According to an exemplary embodiment, the motion information may represent the amount of motion of a surface forming the object. Operation 1720 may be performed by the controller 620 of the tomography apparatus 600.

Lastly, a target image showing the object at a target time point is reconstructed by using the motion information (operation 1730). According to an exemplary embodiment, the target image may be reconstructed based on first and second reconstructed images that are respectively generated based on tomography data acquired during rotation of the first and second X-ray generators by using the motion information. Then, the target image may be reconstructed by performing image registration between the first and second reconstructed images. Operation 1730 may be performed by the image reconstructor 630 of the tomography apparatus 600.

The above-described exemplary embodiments of the present disclosure may be written as computer programs and may be implemented in general-use digital computers that execute the programs using a computer-readable recording medium.

Examples of the computer-readable recording medium include magnetic storage media (e.g., ROM, floppy disks, hard disks, etc.), optical recording media (e.g., CD-ROMs, or DVDs), etc.), and transmission media such as Internet transmission media.

While the present disclosure has been particularly shown and described with reference to exemplary embodiments thereof, it will be understood by those of ordinary skill in the art that various changes in form and details may be made therein without departing from the spirit and scope of the present disclosure as defined by the following claims.

The exemplary embodiments may be written as computer programs and may be implemented in general-use digital computers that execute the programs using a computer-readable recording medium.

Examples of the computer-readable recording medium include magnetic storage media (e.g., ROM, floppy disks, hard disks, etc.), optical recording media (e.g., CD-ROMs, or DVDs), etc.

While one or more exemplary embodiments have been described with reference to the figures, it will be understood by those of ordinary skill in the art that various changes in form and details may be made therein without departing from the spirit and scope as defined by the following claims.

What is claimed is:

1. A tomography apparatus comprising at least one processor configured to:
   obtain a first image using first tomography data acquired as a first X-ray generator for generating X-rays having a first energy rotates around an object over a first angular range, and to obtain a second image using second tomography data acquired as a second X-ray generator for generating X-rays having a second energy rotates around the object over a second angular range different from the first angular range;
   determine motion information representing an amount of motion of the object over time using the first image and the second image; and
   reconstruct a target image showing the object at a target time point using the motion information.

2. The tomography apparatus of claim 1, wherein the first image and the second image are partial images, and the first angular range is opposite to the second angular range.

3. The tomography apparatus of claim 1, wherein each of the first angular range and the second angular range is less than 180 degrees.

4. The tomography apparatus of claim 1, wherein the motion information comprises information representing an amount of motion of a surface forming the object.

5. The tomography apparatus of claim 1, wherein the at least one processor is further configured to predict an amount of motion of the object at the target time point based on the motion information, and to reconstruct the target image based on the predicted amount of motion.

6. The tomography apparatus of claim 1, wherein the at least one processor is further configured to acquire two pieces of tomography data corresponding to an angular range of 180 degrees and an extra angle by respectively using the first x-ray generator and the second X-ray generator,
   wherein the extra angle is in a range of 30 degrees to 70 degrees.

7. The tomography apparatus of claim 1, wherein the at least one processor is further configured to reconstruct the target image based on a first reconstructed image and a second reconstructed image, the first reconstructed image and the second reconstructed image being generated based on the first tomography data and the second tomography data acquired during the rotation of the first x-ray generator and the second X-ray generator using the motion information.

8. The tomography apparatus of claim 7, wherein the at least one processor is further configured to reconstruct the target image by performing image registration between the first reconstructed image and the second reconstructed image.

9. A tomography apparatus comprising at least one processor configured to:
   obtain a first partial image using first tomography data acquired as a first X-ray generator for generating X-rays having a first energy and a second X-ray generator for generating X-rays having a second energy rotate around an object over a first angular range and a second angular range different from the first angular range, and to obtain a second partial image using second tomography data acquired as the first x-ray generator and the second X-ray generator rotate around the object over the second angular range and a third angular range opposite to the first angular range;
   acquire motion information representing an amount of motion of the object over time by using the first partial image and the second partial image; and
   reconstruct a target image showing the object at a target time point by using the motion information.

10. The tomography apparatus of claim 9, wherein each of the first angular range, the second angular range, and the third angular range is less than 180 degrees.

11. The tomography apparatus of claim 9, wherein the first x-ray generator is spaced apart from the second X-ray generator by a 90-degree interval.

12. The tomography apparatus of claim 11, wherein the at least one processor is further configured to acquire the first tomography data and the second tomography data as the first x-ray generator and the second X-ray generator rotate around the object by 90 degrees and an extra angle, and
   wherein the extra angle is less than or equal to 90 degrees.

13. The tomography apparatus of claim 9, wherein the at least one processor is further configured to acquire third tomography data corresponding to an angular range of 180 degrees and an extra angle by using the first x-ray generator and the second X-ray generator, and
   wherein the extra angle is in a range of 30 degrees to 70 degrees.

14. The tomography apparatus of claim 9, wherein the at least one processor is further configured to reconstruct the target image based on a first reconstructed image and a second reconstructed image, the first reconstructed image and the second reconstructed image being based on the first tomography data and the second tomography data acquired during rotation of the first x-ray generator and the second X-ray generator using the motion information.

15. The tomography apparatus of claim 14, wherein the at least one processor is further configured to reconstruct the target image by performing image registration between the first reconstructed image and the second reconstructed image.

16. A method of reconstructing a tomography image, the method comprising:
   obtaining a first image using first tomography data acquired as a first X-ray generator for generating X-rays having a first energy rotates around an object over a first angular range, and obtaining a second image using second tomography data acquired as a second X-ray generator for generating X-rays having a second energy rotates around the object over a second angular range different from the first angular range;

determining motion information representing an amount of motion of the object over time by using the first image and the second image; and reconstructing a target image showing the object at a target time point using the motion information.

17. The method of claim 16, wherein the first image and the second image are partial images, and the first angular range is opposite to the second angular range, and wherein each of the first angular range and the second angular range is less than 180 degrees.

18. The method of claim 16, wherein the motion information comprises information representing an amount of motion of a surface forming the object.

19. The method of claim 16, wherein the reconstructing of the target image comprises predicting an amount of motion of the object at the target time point based on the motion information, and reconstructing the target image based on the predicted amount of motion.

20. The method of claim 16, wherein the reconstructing of the target image comprises reconstructing the target image based on a first reconstructed image and a second reconstructed image, the first reconstructed image and the second reconstructed image being generated based on the first tomography data and the second tomography data acquired during rotation of the first x-ray generator and the second X-ray generator using the motion information.

* * * * *